(12) United States Patent
Ranalletta et al.

(10) Patent No.: US 8,784,377 B2
(45) Date of Patent: Jul. 22, 2014

(54) ANTI-TAMPERING APPARATUS AND METHOD FOR DRUG DELIVERY DEVICES

(71) Applicant: Baxa Corporation, Englewood, CO (US)

(72) Inventors: Joseph Vincent Ranalletta, Englewood, CO (US); Brian William Ward, Littleton, CO (US); Timothy Lee Kingsford, Parker, CO (US)

(73) Assignee: Baxter Corporation Englewood, Englewood, CO (US)

( * ) Notice: Subject to any disclaimer, the term of this patent is extended or adjusted under 35 U.S.C. 154(b) by 0 days.

(21) Appl. No.: 13/737,518

(22) Filed: Jan. 9, 2013

(65) Prior Publication Data

US 2013/0190713 A1 Jul. 25, 2013

Related U.S. Application Data

(63) Continuation of application No. 13/045,742, filed on Mar. 11, 2011, now Pat. No. 8,353,869.

(60) Provisional application No. 61/409,466, filed on Nov. 2, 2010.

(51) Int. Cl.
*A61M 5/00* (2006.01)

(52) U.S. Cl.
USPC ........................................................ 604/110

(58) Field of Classification Search
USPC .................................................. 604/110, 111
See application file for complete search history.

(56) References Cited

U.S. PATENT DOCUMENTS

| 559,360 | A | 5/1898 | Carlson |
| 882,550 | A | 3/1908 | Chellis |
| 1,713,043 | A | 5/1929 | Fullerton |
| 2,033,256 | A | 3/1936 | Schacher |
| 2,560,728 | A | 7/1951 | Lee |
| 2,627,470 | A | 2/1953 | Seiferth |
| 2,880,723 | A | 4/1959 | Adams |

(Continued)

FOREIGN PATENT DOCUMENTS

| EP | 0716860 A2 | 6/1996 |
| WO | 2009109312 A1 | 9/2009 |
| WO | 2010034356 A1 | 4/2010 |
| WO | 2010091522 A2 | 8/2010 |

OTHER PUBLICATIONS

Product Information Card by Baxter, Interlink Needle-Less IV Access System, 1 Page.

(Continued)

*Primary Examiner* — Nicholas Lucchesi
*Assistant Examiner* — Diva K Chander
(74) *Attorney, Agent, or Firm* — Marsh Fischmann & Breyfogle LLP

(57) ABSTRACT

An anti-tampering apparatus and method for drug delivery devices provides for the capture of caps in a manner that restricts repositioning of a captured cap onto a corresponding drug delivery device. The anti-tampering apparatus includes one or more retention members to define a capture region for restrainably capturing a cap. The anti-tampering apparatus further locates an obstruction surface thereof to engage a surface of a drug delivery device and thereby restrict recapping of the device by the captured cap. As such, tampering of a drug delivery device is indicated by the absence of a cap captured within the anti-tampering apparatus.

23 Claims, 18 Drawing Sheets

(56) References Cited

U.S. PATENT DOCUMENTS

| | | |
|---|---|---|
| 2,981,432 A | 4/1961 | Flood |
| 2,988,984 A | 6/1961 | Eckert, Jr. et al. |
| 3,200,486 A | 8/1965 | Shields |
| 3,352,445 A | 11/1967 | Cochin |
| 3,527,017 A | 9/1970 | Taylor et al. |
| 3,604,585 A | 9/1971 | Towns |
| 3,651,615 A | 3/1972 | Bohner et al. |
| 3,676,271 A | 7/1972 | Hake et al. |
| 3,736,933 A | 6/1973 | Szabo |
| 3,807,467 A | 4/1974 | Tascher et al. |
| 3,823,818 A | 7/1974 | Shaw |
| 3,835,897 A | 9/1974 | Gess |
| 3,848,485 A | 11/1974 | Grenci |
| 3,865,236 A | 2/1975 | Rycroft |
| 3,878,026 A | 4/1975 | Snyder et al. |
| 3,880,211 A | 4/1975 | Gess |
| 3,898,861 A | 8/1975 | McMillin |
| 3,935,883 A | 2/1976 | Stach et al. |
| 3,965,945 A | 6/1976 | Ross |
| 4,058,121 A | 11/1977 | Choksi et al. |
| 4,130,149 A | 12/1978 | Hausam |
| 4,195,526 A | 4/1980 | Amos et al. |
| 4,420,092 A | 12/1983 | Finkelstein |
| 4,462,501 A | 7/1984 | Franchi |
| 4,472,357 A | 9/1984 | Levy et al. |
| 4,501,306 A | 2/1985 | Chu et al. |
| 4,502,616 A | 3/1985 | Meierhoefer |
| 4,505,400 A | 3/1985 | Bennett |
| 4,512,472 A | 4/1985 | Jaerund |
| 4,512,475 A | 4/1985 | Federighi |
| 4,535,820 A | 8/1985 | Raines |
| 4,546,901 A | 10/1985 | Buttarazzi |
| 4,586,546 A | 5/1986 | Mezei et al. |
| 4,621,744 A | 11/1986 | Foster |
| 4,624,148 A | 11/1986 | Averette |
| 4,639,250 A | 1/1987 | Rycroft |
| 4,667,837 A * | 5/1987 | Vitello et al. ............... 215/228 |
| 4,674,652 A | 6/1987 | Aten et al. |
| 4,683,916 A | 8/1987 | Raines |
| 4,699,186 A | 10/1987 | Palin et al. |
| 4,699,286 A | 10/1987 | Nolan |
| 4,702,788 A | 10/1987 | Okui |
| 4,758,230 A | 7/1988 | Rycroft |
| 4,773,285 A | 9/1988 | Dionne |
| 4,811,856 A | 3/1989 | Fischman |
| 4,823,982 A | 4/1989 | Aten et al. |
| 4,854,355 A | 8/1989 | Chazot et al. |
| 4,861,335 A | 8/1989 | Reynolds |
| 4,865,592 A | 9/1989 | Rycroft |
| 4,944,736 A | 7/1990 | Holtz |
| 4,974,617 A | 12/1990 | Simon |
| 5,004,962 A | 4/1991 | Fonss et al. |
| 5,012,845 A | 5/1991 | Averette |
| 5,019,048 A | 5/1991 | Margolin |
| 5,040,437 A | 8/1991 | Mueller |
| 5,082,502 A | 1/1992 | Lee et al. |
| 5,083,672 A | 1/1992 | Lewandowski |
| 5,115,949 A | 5/1992 | Rosenthal |
| 5,116,758 A | 5/1992 | Verma |
| 5,123,561 A | 6/1992 | Gross |
| 5,124,434 A | 6/1992 | O'Brien |
| 5,125,748 A | 6/1992 | Bjornson et al. |
| 5,147,054 A | 9/1992 | Pehr |
| 5,170,900 A | 12/1992 | Manera |
| 5,178,684 A | 1/1993 | Hutchins, Sr. |
| 5,188,696 A | 2/1993 | Good, Jr. |
| 5,208,762 A | 5/1993 | Charhut et al. |
| 5,229,074 A | 7/1993 | Heath et al. |
| 5,256,154 A | 10/1993 | Liebert et al. |
| 5,288,285 A | 2/1994 | Carter |
| 5,309,959 A | 5/1994 | Shaw et al. |
| 5,328,474 A | 7/1994 | Raines |
| 5,337,636 A | 8/1994 | Shea |
| 5,337,919 A | 8/1994 | Spaulding et al. |
| 5,341,854 A | 8/1994 | Zezulka et al. |
| 5,356,393 A | 10/1994 | Haber et al. |
| 5,363,885 A | 11/1994 | McConnell et al. |
| 5,380,296 A | 1/1995 | Smedley et al. |
| 5,405,034 A | 4/1995 | Mittel, Jr. |
| 5,427,260 A | 6/1995 | Mueller et al. |
| 5,431,201 A | 7/1995 | Torchia et al. |
| 5,431,299 A | 7/1995 | Brewer et al. |
| 5,451,528 A | 9/1995 | Raymoure et al. |
| 5,453,246 A | 9/1995 | Nakayama et al. |
| 5,479,969 A | 1/1996 | Hardie et al. |
| 5,496,288 A | 3/1996 | Sweeney |
| 5,511,594 A | 4/1996 | Brennan et al. |
| 5,535,785 A | 7/1996 | Werge et al. |
| 5,542,935 A | 8/1996 | Unger et al. |
| 5,591,188 A | 1/1997 | Waisman |
| 5,593,267 A | 1/1997 | McDonald et al. |
| 5,597,530 A | 1/1997 | Smith et al. |
| 5,611,430 A | 3/1997 | Albrecht et al. |
| 5,620,427 A | 4/1997 | Werschmidt et al. |
| 5,632,394 A | 5/1997 | Mecca et al. |
| 5,647,409 A | 7/1997 | Christ et al. |
| 5,651,775 A | 7/1997 | Walker et al. |
| 5,669,599 A | 9/1997 | Toh et al. |
| 5,685,845 A | 11/1997 | Grimard |
| 5,687,885 A | 11/1997 | Turk et al. |
| 5,702,374 A | 12/1997 | Johnson |
| 5,704,921 A | 1/1998 | Carilli |
| 5,735,181 A | 4/1998 | Anderson |
| 5,753,451 A | 5/1998 | Smith |
| 5,755,894 A | 5/1998 | Bowman et al. |
| 5,756,178 A | 5/1998 | Obadia |
| 5,769,086 A | 6/1998 | Ritchart et al. |
| 5,775,671 A | 7/1998 | Cote, Sr. |
| 5,782,157 A | 7/1998 | Ellington et al. |
| 5,785,691 A | 7/1998 | Vetter et al. |
| 5,788,215 A | 8/1998 | Ryan |
| 5,805,454 A | 9/1998 | Valerino, Sr. et al. |
| 5,807,345 A | 9/1998 | Grabenkort |
| 5,826,409 A | 10/1998 | Slepicka et al. |
| 5,829,610 A | 11/1998 | Rohr et al. |
| 5,851,201 A | 12/1998 | Ritger et al. |
| 5,855,230 A | 1/1999 | Guala et al. |
| 5,855,839 A | 1/1999 | Brunel |
| 5,883,370 A | 3/1999 | Walker et al. |
| 5,884,457 A | 3/1999 | Ortiz et al. |
| 5,887,722 A | 3/1999 | Albrecht et al. |
| 5,893,259 A | 4/1999 | Posge |
| 5,899,889 A | 5/1999 | Futagawa et al. |
| 5,900,557 A | 5/1999 | Tanihata et al. |
| 5,911,252 A | 6/1999 | Cassel |
| 5,915,089 A | 6/1999 | Stevens et al. |
| 5,947,954 A | 9/1999 | Bonaldo |
| 5,948,360 A | 9/1999 | Rao et al. |
| 5,954,313 A | 9/1999 | Ryan |
| 5,984,373 A | 11/1999 | Fitoussi et al. |
| 5,985,038 A | 11/1999 | Dawson |
| 5,989,227 A | 11/1999 | Vetter et al. |
| RE36,557 E | 2/2000 | Brown |
| 6,027,472 A | 2/2000 | Kriesel et al. |
| 6,033,911 A | 3/2000 | Schultz et al. |
| 6,039,302 A | 3/2000 | Cote, Sr. et al. |
| 6,048,086 A | 4/2000 | Valerino, Sr. |
| 6,063,062 A | 5/2000 | Paradis |
| 6,068,614 A | 5/2000 | Kimber et al. |
| 6,142,039 A | 11/2000 | Herring, Sr. |
| 6,152,913 A | 11/2000 | Feith et al. |
| 6,158,458 A | 12/2000 | Ryan |
| 6,171,287 B1 | 1/2001 | Lynn et al. |
| 6,193,688 B1 | 2/2001 | Balestracci et al. |
| 6,200,289 B1 | 3/2001 | Hochman et al. |
| 6,202,923 B1 | 3/2001 | Boyer et al. |
| 6,217,560 B1 | 4/2001 | Ritger et al. |
| 6,226,745 B1 | 5/2001 | Wiederhold |
| 6,240,952 B1 | 6/2001 | Schroeder |
| 6,267,154 B1 | 7/2001 | Felicelli et al. |
| RE37,357 E | 9/2001 | Lynn |
| 6,332,633 B1 | 12/2001 | Fitoussi et al. |
| 6,343,690 B1 | 2/2002 | Britton et al. |
| 6,360,794 B1 | 3/2002 | Turner |

(56) References Cited

U.S. PATENT DOCUMENTS

| | | | |
|---|---|---|---|
| 6,394,983 B1 | 5/2002 | Mayoral et al. | |
| 6,439,442 B1 | 8/2002 | Markert et al. | |
| 6,485,460 B2 | 11/2002 | Eakins et al. | |
| 6,491,667 B1 | 12/2002 | Keane et al. | |
| 6,520,935 B1 * | 2/2003 | Jansen et al. | 604/111 |
| 6,585,691 B1 | 7/2003 | Vitello | |
| 6,599,476 B1 | 7/2003 | Watson et al. | |
| 6,604,903 B2 | 8/2003 | Osborne et al. | |
| 6,615,881 B2 | 9/2003 | Bartholomew et al. | |
| 6,616,771 B2 | 9/2003 | Osborne et al. | |
| 6,623,455 B2 | 9/2003 | Small et al. | |
| 6,722,404 B2 | 4/2004 | Osborne | |
| 6,726,652 B2 | 4/2004 | Eakins et al. | |
| 6,783,031 B2 | 8/2004 | Robbins et al. | |
| 6,813,868 B2 * | 11/2004 | Baldwin et al. | 53/411 |
| 6,821,268 B2 | 11/2004 | Balestracci | |
| 6,846,303 B2 | 1/2005 | Eakins et al. | |
| 6,877,530 B2 * | 4/2005 | Osborne et al. | 141/27 |
| 6,915,823 B2 | 7/2005 | Osborne et al. | |
| 6,921,383 B2 | 7/2005 | Vitello | |
| 6,942,643 B2 | 9/2005 | Eakins et al. | |
| 6,986,234 B2 | 1/2006 | Liedtke | |
| 6,988,642 B2 | 1/2006 | Gallo et al. | |
| 6,991,002 B2 | 1/2006 | Osborne et al. | |
| 7,007,443 B2 * | 3/2006 | Liedtke et al. | 53/399 |
| 7,017,622 B2 | 3/2006 | Osborne et al. | |
| 7,017,623 B2 | 3/2006 | Tribble et al. | |
| 7,025,098 B2 | 4/2006 | Osborne | |
| 7,096,212 B2 | 8/2006 | Tribble et al. | |
| 7,114,619 B2 | 10/2006 | Ellis et al. | |
| 7,163,114 B2 | 1/2007 | Okiyama | |
| 7,214,214 B2 | 5/2007 | Sudo et al. | |
| 7,223,259 B2 | 5/2007 | Marshall et al. | |
| 7,240,699 B2 | 7/2007 | Osborne et al. | |
| 7,370,773 B2 | 5/2008 | Toth et al. | |
| 7,481,339 B1 | 1/2009 | Hsu | |
| 7,530,974 B2 | 5/2009 | Domkowski et al. | |
| 7,632,244 B2 * | 12/2009 | Buehler et al. | 604/111 |
| 7,762,988 B1 | 7/2010 | Vitello | |
| 2001/0018937 A1 | 9/2001 | Nemoto | |
| 2001/0047976 A1 | 12/2001 | Frank | |
| 2002/0020459 A1 | 2/2002 | Baldwin et al. | |
| 2002/0188467 A1 | 12/2002 | Eke | |
| 2002/0198738 A1 | 12/2002 | Osborne | |
| 2003/0033532 A1 | 2/2003 | Marks | |
| 2004/0001906 A1 | 1/2004 | Carhuff et al. | |
| 2004/0088187 A1 | 5/2004 | Chudy et al. | |
| 2004/0088951 A1 | 5/2004 | Baldwin et al. | |
| 2004/0225258 A1 * | 11/2004 | Balestracci | 604/111 |
| 2004/0236630 A1 | 11/2004 | Kost et al. | |
| 2004/0250842 A1 | 12/2004 | Adams et al. | |
| 2005/0045242 A1 | 3/2005 | Osborne | |
| 2005/0224137 A1 | 10/2005 | Tribble et al. | |
| 2005/0252572 A1 | 11/2005 | Khan et al. | |
| 2006/0138145 A1 | 6/2006 | Toth et al. | |
| 2006/0178578 A1 | 8/2006 | Tribble et al. | |
| 2007/0043767 A1 | 2/2007 | Osborne et al. | |
| 2007/0278140 A1 | 12/2007 | Mallett et al. | |
| 2008/0097310 A1 * | 4/2008 | Buehler et al. | 604/111 |
| 2009/0082725 A1 | 3/2009 | Witowski | |
| 2010/0268169 A1 | 10/2010 | Llewellyn-Hyde et al. | |

OTHER PUBLICATIONS

Information Page by Baxter, Interlink Needle-Less IV Access System, www.life-assist.com, 37 Pages.

International Standard (ISO) 594/1 Conical fittings with a 6% (Luer) taper for syringes, needles and certain other medical equipment—Part 1: General requirements, Ref. No. ISO 954/1-1986 (E).

International Standard (ISO) 594/2 Conical fittings with 6% (Luer) taper for syringes, needles and certain other medical equipment—Part 2: Lock fittings, Ref. No. ISO 954-2: 1998 (E).

* cited by examiner

ANTI-TAMPERING APPARATUS AND METHOD FOR DRUG DELIVERY DEVICES

RELATED APPLICATIONS

This application is a continuation application of U.S. patent application Ser. No. 13/045,742 filed Mar. 11, 2011, which claims the benefit of U.S. Provisional Application No. 61/409,466, filed Nov. 2, 2010, entitled "ANTI-TAMPERING APPARATUS AND METHOD FOR DRUG DELIVERY DEVICES", both of which are hereby incorporated by reference in their entirety.

FIELD OF THE INVENTION

The present invention relates to drug delivery devices, and more particularly, to an anti-tampering apparatus and method for use with drug delivery devices. The invention is particularly apt for use with drug delivery devices, such as syringes and oral dispensers, after filling with a liquid medication.

BACKGROUND OF THE INVENTION

Drug delivery devices are commonly used to hold and deliver prescribed quantities of medication to a patient. Exemplary drug delivery devices include, but are not limited to syringes, oral syringes, vials and other capped containers that function to hold and deliver a prescribed and precise amount of liquid medication to a patient.

Once filled with a liquid medication and capped, it is important that the drug delivery device be provided to a patient care site for administration to the intended patient with the integrity of the contents thereof uncompromised. Further, in the event that the drug delivery device is not used at a patient care site, it may be important that the drug delivery device be returned (e.g., to a pharmacy) so that the contents thereof may be handled in an appropriate manner. Such considerations are particularly important when certain medical liquids, such as narcotic drugs, are being handled.

In this regard, numerous approaches have been proposed for indicating when a drug delivery device has been tampered with prior to or otherwise apart from intended patient administration. One approach that has been proposed for use in conjunction with syringes is a break-away, colored sleeve that caps a syringe. The colored sleeves may be divided and arranged in a tray prior to being mated with syringes such that a user may cap the syringe directly by inserting the end of the syringe to be capped into one selected colored sleeve that is in the tray, resulting in the colored cap being securely attached to the end. If the syringe is tampered with and the contents are accessed through the capped end, the colored sleeve will be broken, thereby providing a visual indicator that the syringe has been tampered with. In another approach, an open end of a syringe may be capped with a shell that is constructed such that tampering with the syringe results in the shell being broken-away in a manner that provides a visual indicator that the syringe has been tampered with.

In each of the noted approaches, as well as additional approaches that have been proposed, visual indications are relied upon to identify the occurrence of tampering. In such approaches, recapping of a tampered syringe is not restricted, only indicated upon visual inspection.

SUMMARY OF THE INVENTION

One objective of the present invention is to provide an improved anti-tampering apparatus and method that restricts recapping of a drug delivery device together with the anti-tampering apparatus.

Another objective of the present invention is to provide an improved anti-tampering apparatus and method that is user-friendly.

Yet another objective of the present invention is to provide an improved anti-tampering apparatus and method for drug delivery devices that may be implemented in a cost effective manner.

One or more of the above objectives and additional advantages may be realized by an anti-tampering apparatus and method comprising the present invention.

In one embodiment, an anti-tampering apparatus is provided that includes a frame member. The apparatus further includes at least one retention member connected to the frame member for non-removable capture of a cap disposed on a port of a corresponding drug delivery device (e.g., a syringe, an oral dispenser, or other like devices filled with a liquid medication for patient administration). The frame may define an internal or encompassed area having an opening, wherein the retention member(s) may extend into the internal area to define a cap capture region spaced rearward from the opening.

The anti-tampering apparatus may be provided so that a cap captured within the apparatus is restricted from replacement on a corresponding drug delivery device port after initial removal therefrom. As may be appreciated, the absence of a captured cap on a drug delivery device and/or the presence of a cap without the anti-tampering apparatus properly interconnected thereto provides a user with an immediate and easily perceptible indication that tampering may have occurred.

In one aspect, the anti-tampering apparatus may include an obstruction surface for obstructing replacement of a captured cap back onto a port of a corresponding drug delivery device after initial removal therefrom. In one approach, the obstruction surface may be located on the frame member of the anti-tampering apparatus. By way of example, the obstruction surface may be presented on a peripheral edge of a cylindrical end portion of the frame member. In other approaches, the obstruction surface may be provided on the cap retention member(s).

In another approach, the anti-tampering apparatus may include at least one pivot member connected to the frame, wherein the pivot member(s) pivots from a first position to a second position when a cap disposed on a drug delivery device is positioned within the capture region. In turn, the obstruction surface may be provided on the pivot member when the captured cap is removed from the drug delivery device.

In one embodiment, the pivot member may comprise a first portion and a second portion, wherein a cap disposed on a corresponding drug delivery device may engage the first portion upon positioning within the capture region and, in response to such engagement, the second portion may pivot from a first position to a second position. In the second position, the second portion may be in spring-loaded engagement with a portion of the drug delivery device. For example, at least one of the pivot member (e.g., the second portion thereof) and the frame may elastically deform when the pivot member is moved to the second position (e.g., in response to engagement with a portion of the drug delivery device). In turn, upon removal of the captured cap from the drug delivery device, the second portion may automatically advance inward to present an obstruction surface.

In various embodiments, a cap disposed on a drug delivery device port may be forcibly advanced in a first direction past the retention member(s) into the capture region. In this regard, at least a portion of the retention member(s) and/or frame and/or cap may flex, or elastically deform, during advancement and cap capture. Upon cap capture, the captured cap may be restrained from movement in an opposite second direction by the retention member(s).

By way of example, the retention member(s) may comprise a detent(s) projecting inward (e.g., into the internal area) from a wall of the frame member. In some implementations, the detent(s) may be of a barbed configuration having a tapered first surface extending inward from the wall and away from the opening, and a second surface, or ledge, for restrainably engaging a cap captured by the anti-tampering apparatus. In various arrangements, a plurality of retention members (e.g., three or more detents or segments or sets of detents) may be spaced (e.g., at equidistances relative to each other and from the opening) about an internal wall of the frame.

In contemplated embodiments, the anti-tampering apparatus may be provided so that a length of the capture region is greater than a length of the cap captured by the anti-tampering apparatus. Further, the capture region may be sized to permit a captured cap to move rearwardly within the capture region.

To facilitate cap capture in various embodiments, the retention member(s) may be provided to define a minimum cross-dimension within the internal area that is less than a maximum cross-dimension of the cap. In some implementations, the retention member(s) may be provided to define a reduced opening (e.g., a segmented circular opening) within the internal area having a diameter that is less than a maximum diameter of a cap (e.g., a cap having a circular periphery at its maximum cross-dimension). By way of example, a plurality of retention member(s) may extend into the internal area from a wall of the frame to define minimum cross-dimension and/or a reduced opening having a diameter that is less than a maximum cross-dimension and/or maximum diameter of a cap, respectively.

In some embodiments, the anti-tampering apparatus may be provided with an end wall at an opposite end from the opening. By way of example, the end wall may be provided at a rearward end of the capture region.

As may be appreciated, an inventive method is also provided. In one embodiment, a method is provided for handling a drug delivery device having a port, and a corresponding cap positionable on the port, such method including the steps of capturing a cap disposed on a port of a drug delivery device within an anti-tampering apparatus, and removing the cap from the port of said drug delivery device, wherein the anti-tampering apparatus maintains capture of the cap. The embodiment may further include the step of restricting repositioning of the captured cap onto the port of the corresponding drug delivery device.

In some embodiments, the capturing step may include advancing at least a portion of the cap forcibly passed at least one retention member(s) provided on the anti-tampering apparatus, wherein the cap is restrainably disposed within a captured region of the anti-tampering apparatus. In conjunction with such advancement and cap capture, the method may further include resiliently flexing at least a portion of at least one of the cap and the anti-tampering apparatus. By way of example, at least a portion of one or a plurality of retention member(s) and/or a portion of an interconnected frame of the anti-tampering apparatus may flex in conjunction with forcible advancement of a cap into the captured region relative thereto. Alternatively and/or additionally, a portion of the cap (e.g., sidewall portions thereof) may flex in conjunction with forcible advancement of the cap relative to the anti-tampering apparatus.

In relation to the restrictive step of the method embodiment, at least one obstruction surface may be provided on the anti-tampering apparatus. The obstruction surface may be located to engage a surface of the drug delivery device and thereby obstruct repositioning of the cap on the post of the drug delivery device after removal of the cap therefrom. In various embodiments, the obstruction surface may be provided by a frame of the anti-tampering apparatus. In other embodiments, the obstruction surface may be provided on one or members interconnected to a frame of the anti-tampering apparatus. In some implementations, the obstructive surface(s) may be located in an initial position prior to the capturing step and automatically located in an obstruction position different from the initial position after the removing step.

In this regard, the method may include first moving an obstruction surface(s) from an initial position to another position in response to the capturing step, and second moving the obstruction surface(s) from the another position to the obstruction position in response to the removing step. In one approach, the obstruction surface(s) may be located on a pivot member(s) interconnected to a frame of the anti-tampering apparatus. In turn, the method may include pivoting the one pivot member(s) relative to the frame to at least partially reposition the obstruction surface(s) from the initial position to the obstruction position in response to the capturing step. In some embodiments, the pivot member(s) may engage the drug delivery device upon cap capture and at least a port of the pivot member(s) may and/or the frame may be provided to elastically deform prior to removal of the captured cap from the drug delivery device. In turn, upon such removal the pivot member(s) may move inward to present the obstruction surface(s).

In certain implementations, a method embodiment may include the additional step of filling the drug delivery device with a predetermined amount of liquid medication prior to the capturing, removing and restricting steps. By way of example, the filling step may be completed at a medical liquid dispensary (e.g., a pharmacy) of a medical care facility. As may be appreciated, drug delivery devices may be filled at such locations on a patient and/or drug specific basis, wherein after filling the drug delivery devices may be transported to specific patient care locations at the facility for administration to a given patient by medical personnel.

The method embodiment may further include the step of positioning the cap on the port of the drug delivery device after filling and prior to the capturing, removing and restricting steps. In some implementations, one or more of the filling, positioning and capturing steps may be completed in an automated manner. By way of example, each of the filling, positioning and capturing steps may be automated. In one approach, one or more of such steps may be completed utilizing methods and apparatus taught in U.S. Pat. Nos. 6,915,823; 6,991,002; 7,017,622; 7,017,623; 7,117,902; 7,814,731; and U.S. Patent Application Publication Nos. 2007/0125442; 2008/0169043; 2008/0169044; 2008/0169045; and 2009/0154764, hereby incorporated by reference their entirety.

In one embodiment, a drug delivery device and corresponding cap may be packaged in the same or separate enclosures. Further, a corresponding anti-tampering apparatus may be packaged in the same or a separate enclosure. In this regard, the drug delivery device and a plurality of like drug delivery devices may be packaged in a common enclosure. Similarly, the cap and a plurality of like caps may be packaged in a common enclosure, and the anti-tampering apparatus and a plurality of like anti-tampering apparatus may be packaged in a common enclosure. In some implementations, the plurality of drug delivery devices and/or corresponding caps and/or corresponding anti-tampering apparatus may be packaged in a common enclosure.

The above-noted packaging may be completed at a first location. By way of example, the first location may correspond with a production or assembly facility for the drug delivery device(s) and corresponding cap(s). In conjunction with such packaging, the drug delivery device(s) and cap(s) may be sterilized at the first location (e.g., prior to or after packaging).

The method embodiment may include transporting the above-noted enclosure(s) from the first location to a second location, remote from the first location. By way of primary example, the second location may be a medical dispensary for a medical care facility. In particular, the second location may correspond with a pharmacy for a hospital or other patient care facility.

In turn, the method embodiment may include unpackaging the drug delivery device(s) and cap(s) at the second location. Then, after unpackaging, the method may provide for completing the filling, positioning (e.g., capping), capturing, removing and restricting steps at the second location. For example, the filling and positioning steps may be completed in a clean and sterile environment, and may be completed manually or in an automated fashion. Similarly, the capturing step may be completed in a sterile or otherwise clean environment either manually or in an automated manner.

In conjunction with such implementations, the method embodiment may further include the step of providing an anti-tampering apparatus separate and/or with a plurality of like anti-tampering apparatus to the second location, separate from the packaged enclosure(s) of drug delivery devices and caps. The anti-tampering apparatus may be packaged at the same first location as the drug delivery devices and caps, or at a different site, and transported to the second location. In this regard, production, assembly and/or packaging of the anti-tampering apparatus may be completed utilizing the same or different procedures than those implemented in relation to the drug delivery device(s) and cap(s).

Numerous additional features and advantages of the present invention will become apparent to those skilled in the art upon consideration of the embodiment descriptions provided hereinbelow.

DETAILED DESCRIPTION

Figure 1:
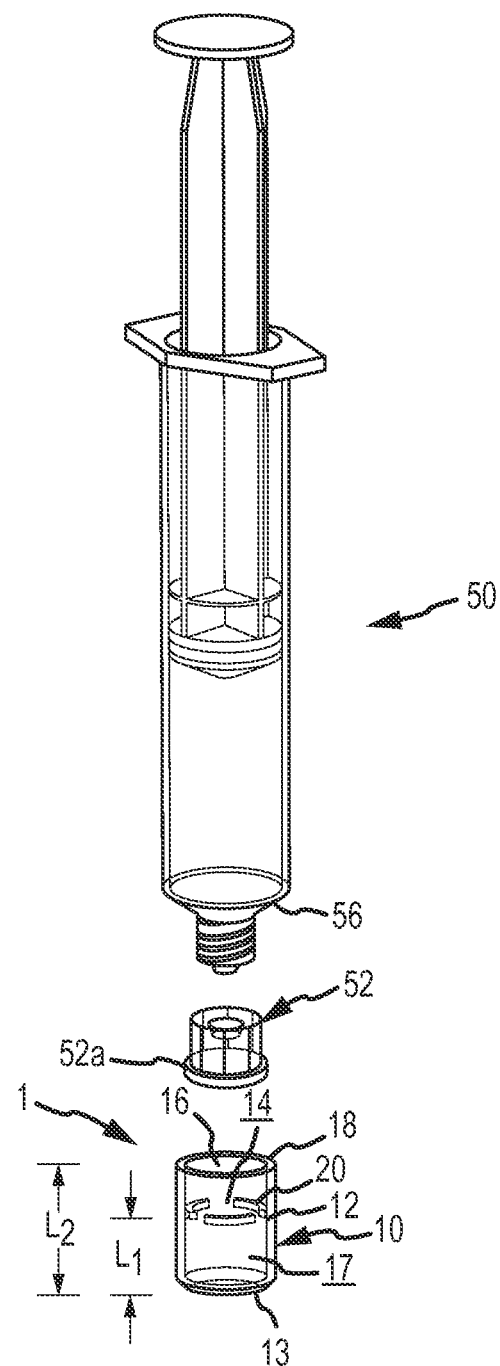
FIG. 1 illustrates one embodiment of an anti-tampering apparatus provided for use with a syringe and corresponding cap.

FIGS. 1-6 correspond with one embodiment of an anti-tampering apparatus 1. The anti-tampering apparatus 1 is provided for use with a drug delivery device comprising a syringe 50 (e.g., a luer lock syringe) and a slip-on cap 52 intended for positioning on port 54 of syringe 50. More particularly, the anti-tampering apparatus 1 is provided to restrainably retain, or capture, cap 52. In one application, the syringe 50 may be filled with a drug in a liquid form prior to cap 52 capture by anti-tampering apparatus 1.

The anti-tampering apparatus 1 may comprise a frame member 10. Optionally, and as shown, frame member 10 may be at least partially transparent. The anti-tampering apparatus 1 may further include one or more retention member(s) 20 connected to the frame member 10 and disposed to capture cap 52. By way of example, the retention member(s) 20 may be configured as a detent(s) projecting inwardly from a sidewall 12 of the frame member 10. In the illustrated embodiment three (3) segments of detent members may be spaced about the sidewall 12 (e.g., at equal distances therebetween).

The frame member 10 and retention member(s) 20 may be integrally defined in a unitary anti-tampering apparatus embodiment. For example, anti-tampering apparatus 1 may be injection-molded (e.g., utilizing a collapsible mold) from a polymer-based material. In some embodiments, the anti-tampering apparatus may comprise a polypropylene material or a stiffer polyethylene or polystyrene material.

In the illustrated embodiment, the frame member 10 is configured as a cap, with cylindrical sidewalls 12 and an end wall 13. In other embodiments, the frame member 10 may assume other configurations.

FIG. 1 illustrates the syringe 50 prior to capping of port 54 by cap 52, and prior to capture of cap 52 by anti-tampering apparatus 1. Such capping and capture steps may be sequentially completed, as reflected by FIGS. 2 and 3. Further, such steps may be completed manually and/or in an automated manner by relative linear advancement of cap 52 and port 54 of syringe 50, and by relative linear advancement of capped syringe 50 and anti-tampering apparatus 1. In some applications, such steps may be completed in a single-stroke, linear movement of syringe 50. For example, cap 52 and anti-tampering apparatus 1 may be held in aligned positions (see, e.g., FIG. 1) by a fixture and syringe may be linearly advanced in a first stroke segment to locate cap 52 on port 54. In turn, capped syringe 50 may be linearly advanced in a second stroke segment to capture the cap 52 of the capped syringe 50 within the anti-tampering apparatus 1.

As shown in FIG. 1, the frame member 10 may define an encompassed or internal area 14 having a length $L_2$. Further, the frame member 10 may comprise an opening 16 to the encompassed or internal area 14 for receiving the cap 52 after positioning the cap 52 on the port 54 of syringe 50. In the illustrated embodiment, three (3) retention members 20 may be spaced at equal distances from the opening 16.

Figure 2:
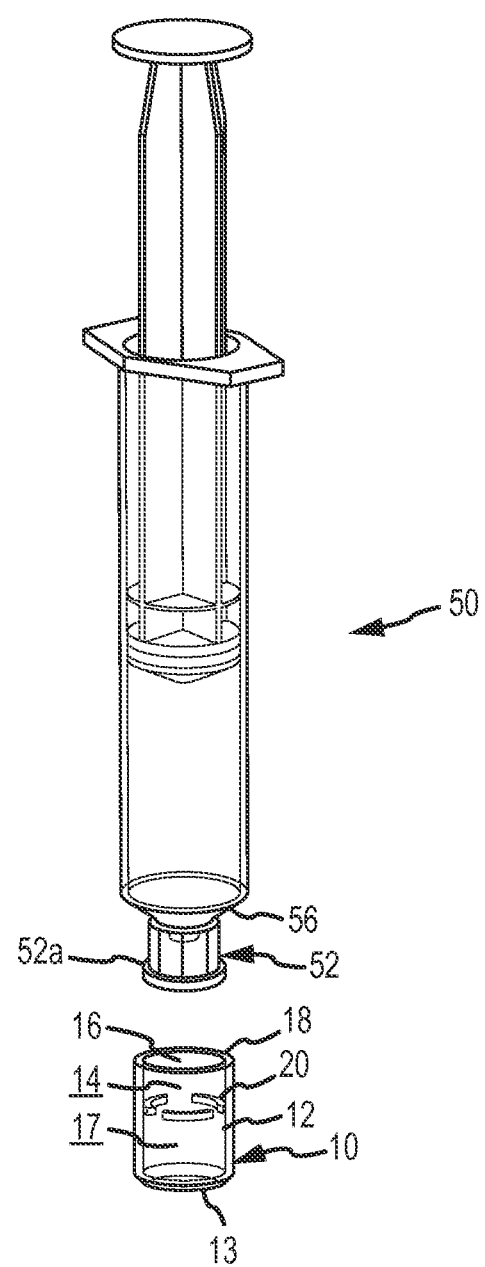
FIG. 2 illustrates the embodiment of FIG. 1 with the cap positioned on the corresponding syringe.
Figure 3A:
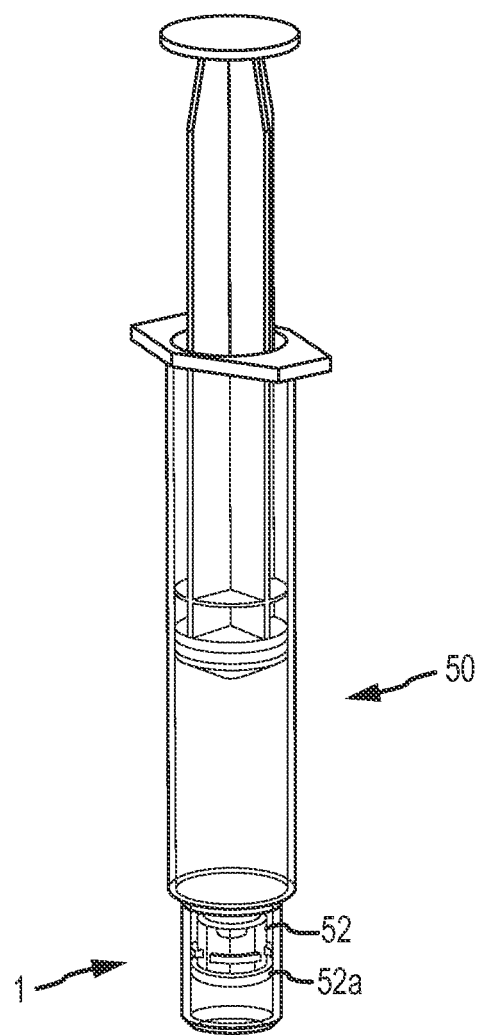
FIGS. 3A and 3B illustrate the embodiment of FIG. 1 with the cap positioned on the syringe captured by the anti-tampering apparatus.
Figure 3B:
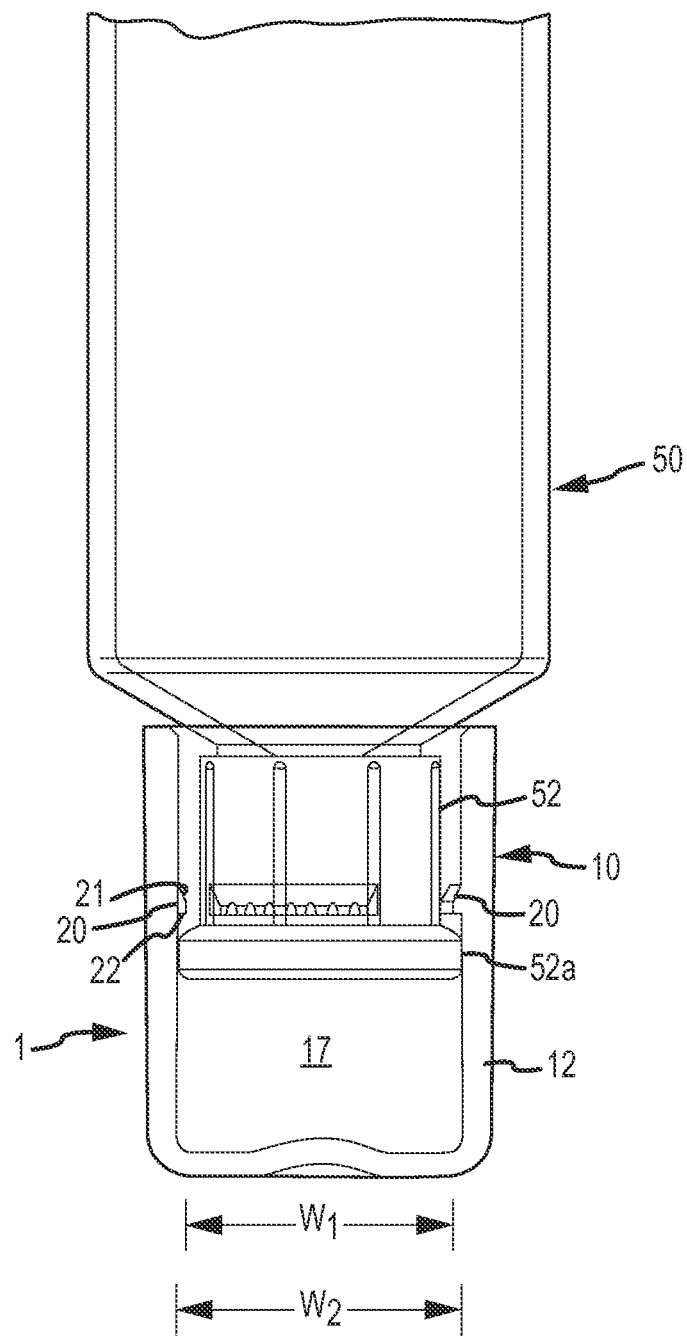

The retention member(s) 20 may define a capture region 17 having a length $L_1$. In this regard, the retention member(s) 20 may be provided so that, after placement of cap 52 on port 54 of syringe 50, as shown in FIG. 2, at least a portion of cap 52 may be forcibly advanced past the retention member(s) 20 in a first direction and retainably captured within the capture region 17, as shown in FIGS. 3A and 3B. In this regard, at least a portion of retention member(s) 20 and/or frame 10 and/or cap 52 may resiliently flex, or elastically deform, during cap capture.

As best shown in FIG. 3B, upon capture of at least a portion of cap 52 the retention member(s) 20 may be located to restrict movement of the cap 52 in a second direction opposite to the first direction. By way of example, retention member(s) 20 may define a minimum cross-dimension $W_1$ within encompassed or internal area 14 that is less than a maximum cross-dimension $W_2$ of cap 52. In the illustrated embodiment, the maximum cross-dimension $W_2$ of cap 52 may be defined by outwardly projecting flange 52a of cap 52.

The retention member(s) 20 may be of a barb-like configuration, wherein the retention member(s) 20 includes a tapered surface 21 and ledge surface 22. The retention member(s) 20 may be disposed to restrainably engage flange 52a of cap 52 at ledge surface 22 when captured cap 52 is moved toward opening 16.

Figure 4A:
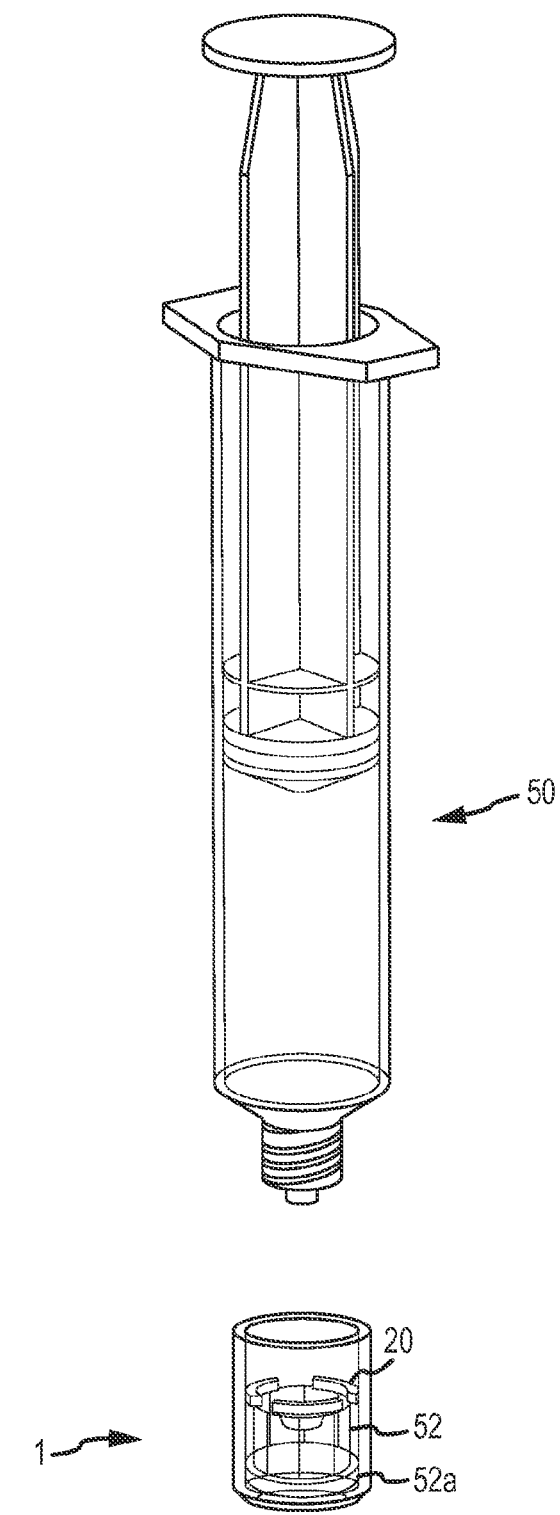
FIGS. 4A and 4B illustrate the embodiment of FIG. 1 with the captured cap removed from the syringe.
Figure 4B:
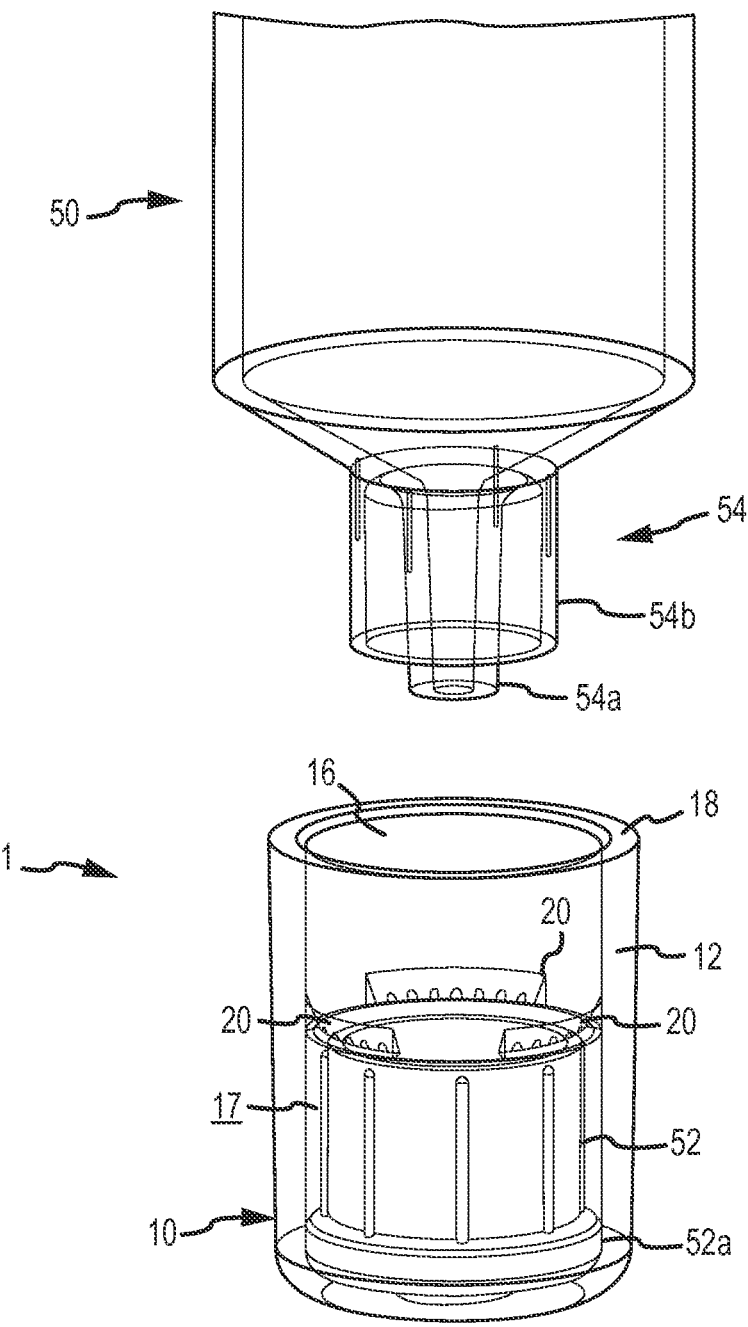

In that regard, upon capture of at least a portion of cap 52 in capture region 17 (e.g., flange 52a), syringe 50 and/or anti-tampering apparatus 1 may be moved relative to the other, e.g., syringe 50 may be retracted in the second direction while anchoring anti-tampering apparatus 1, wherein captured cap 52 may be removed from port 54 of syringe 50, as shown in FIGS. 4A and 4B. In conjunction with removal of cap 52, flange 52a thereof may engage and be restrainably retained within capture region 17 by retention member(s) 20. As may be appreciated, such cap removal may be completed in conjunction with intended procedures in which the liquid drug may be administered from syringe 50 to an intended patient after removal of cap 52.

Figure 5:
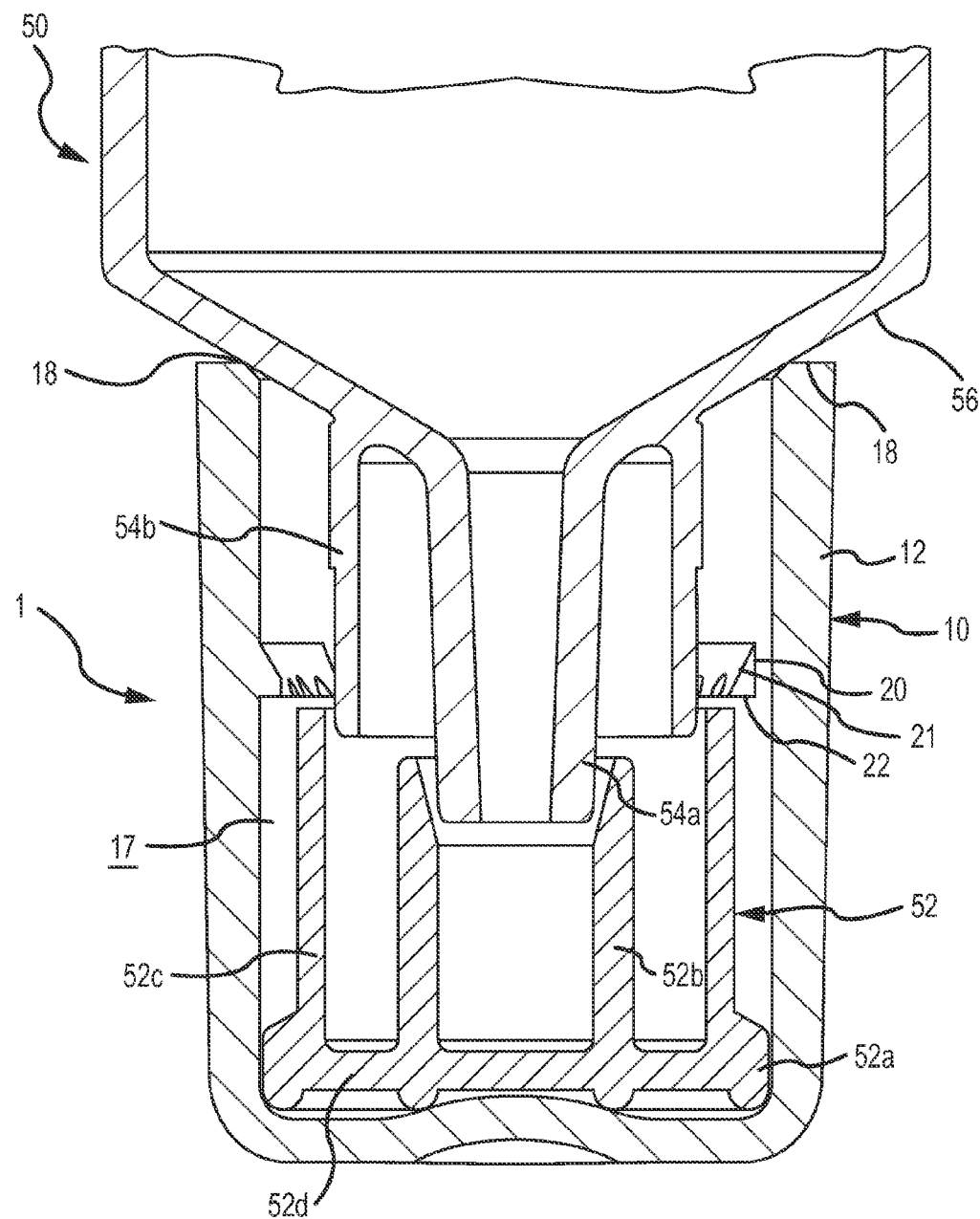
FIG. 5 is a cross-sectional view of the embodiment of FIG. 1, wherein recapping of the syringe is obstructed by the anti-tampering apparatus.

As shown by FIG. 5, the anti-tampering apparatus may be provided so that once cap 52 is captured in capture region 17 of anti-tampering apparatus 1, and cap 52 is removed from port 54 of the syringe 50, the anti-tampering apparatus 1 may obstruct any attempt to recap the port 54 with the captured cap 52. In this regard, the frame member 10 may comprise a cylindrical edge surface 18 surrounding opening 16. The edge surface 18 may be located to obstruct recapping of syringe 50 after capture of cap 52 within the capture region 17 and removal of cap 52 from port 54 of syringe 50. Specifically, after removal of cap 52, edge surface 18 may engage a barrel surface 56 of the syringe 50 to obstruct recapping of port 54. Concomitantly, cap 52 may assume a position in a rearward, or bottom, portion of the capture region 17, as shown in FIG. 5.

In the embodiment shown in FIGS. 1-5, syringe 50 may comprise a barrel (e.g., having volumetric gradations, or indicia, thereupon) and a plunger disposed therein for selective dispensation of predetermined amounts of a liquid drug (e.g., a predetermined unit dosage amounts). Syringe 50 may be of a type having a port 54 adapted for forcible, slip-on placement of cap 52. In this regard, syringe 50 may be of a type having a luer-lock connection arrangement at port 54, as shown in FIGS. 1, 2, 3A and 4A. For example, port 54 may include a nozzle 54a extending through and beyond a surrounding collar 54b having a threaded internal sidewall. In turn, cap 52 may include an annular (e.g., cylindrical) inner collar 52b and an annular (e.g., cylindrical) outer collar 52c extending from an end wall 52d, wherein nozzle 54a may be forcibly advanced in a slip-on fashion into inner collar 52b of cap 52, and outer collar 54b of port 54 may be located in an annular region defined between inner collar 54b and outer collar 52c of cap 52.

Since positioning of cap 52 upon syringe 50 may entail forcible advancement of port 54 relative to cap 52, cap 52 may assume a rearward position in capture region 17 upon any attempt to recap port 54 after removal of cap 52. In conjunction therewith, any attempt to recap the syringe 50 may be frustrated by obstructive engagement between edge surface 18 and barrel surface 56. As such, undesired tampering may be avoided since any unexpected absence of cap 52, as captured by anti-tampering apparatus 1, on port 54 of syringe 50 may provide a definite indication that tampering has occurred.

FIGS. 6-10 correspond with another embodiment of an anti-tampering apparatus 101. The anti-tampering apparatus 101 is provided for use with a drug delivery device comprising an oral syringe 150, or dispenser, and a slip-on cap 152 intended for positioning on port 154 of dispenser 150. More particularly, the anti-tampering apparatus 101 is provided to restrainably retain, or capture, cap 152. In one application, the dispenser 150 may be filled with a drug in a liquid form prior to cap 152 capture by anti-tampering apparatus 101.

The anti-tampering apparatus 101 may comprise a frame member 110. Optionally, and as shown, frame member 110 may be at least partially transparent. The anti-tampering apparatus 101 may further include one or more retention member(s) 120 connected to the frame member 110 and disposed to capture cap 152. By way of example, the retention member(s) 120 may be configured as a detent(s) projecting inwardly from a sidewall 112 of the frame member 110. In the illustrated embodiment three (3) sets of detent members may be spaced about the sidewall 112.

The frame member 110 and retention member(s) 120 may be integrally defined in a unitary anti-tampering apparatus embodiment. For example, anti-tampering apparatus 101 may be injection-molded (e.g., utilizing a collapsible mold) from a polymer-based material. In some embodiments, the anti-tampering apparatus may comprise a polypropylene material or a stiffer polyethylene or polystyrene material.

In the illustrated embodiment, the frame member 110 is configured as a cap, with cylindrical sidewalls 112 and an end wall 113. In other embodiments, the frame member 110 may assume other configurations.

Figure 6:
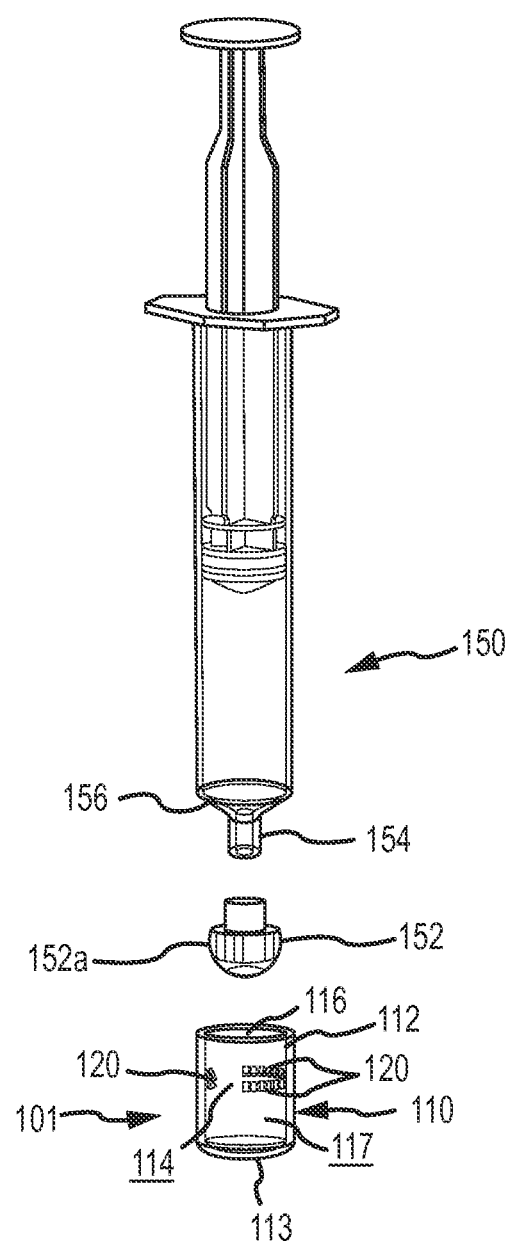
FIG. 6 illustrates another embodiment of an anti-tampering apparatus provided for use with an oral syringe, or dispenser, and corresponding cap.

FIG. 6 illustrates the dispenser 150 prior to capping of port 154 by cap 152, and prior to capture of cap 152 by anti-tampering apparatus 101. Such further capping and capture steps may be sequentially completed, as reflected by FIGS. 7 and 8. Further, such steps may be completed manually and/or in an automated manner by relative linear advancement of cap 152 and port 154 of dispenser 150, and by relative linear advancement of capped syringe 150 and anti-tampering apparatus 101. In some applications, such steps may be completed in a single-stroke, linear movement of dispenser 150. For example, cap 152 and anti-tampering apparatus 101 may be held in aligned positions (see, e.g., FIG. 6) by a fixture and syringe may be linearly advanced in a first stroke segment to locate cap 152 on port 154. In turn, capped dispenser 150 may be linearly advanced in a second stroke segment to capture the cap 152 of the capped syringe 150 within the anti-tampering apparatus 101.

Figure 7:
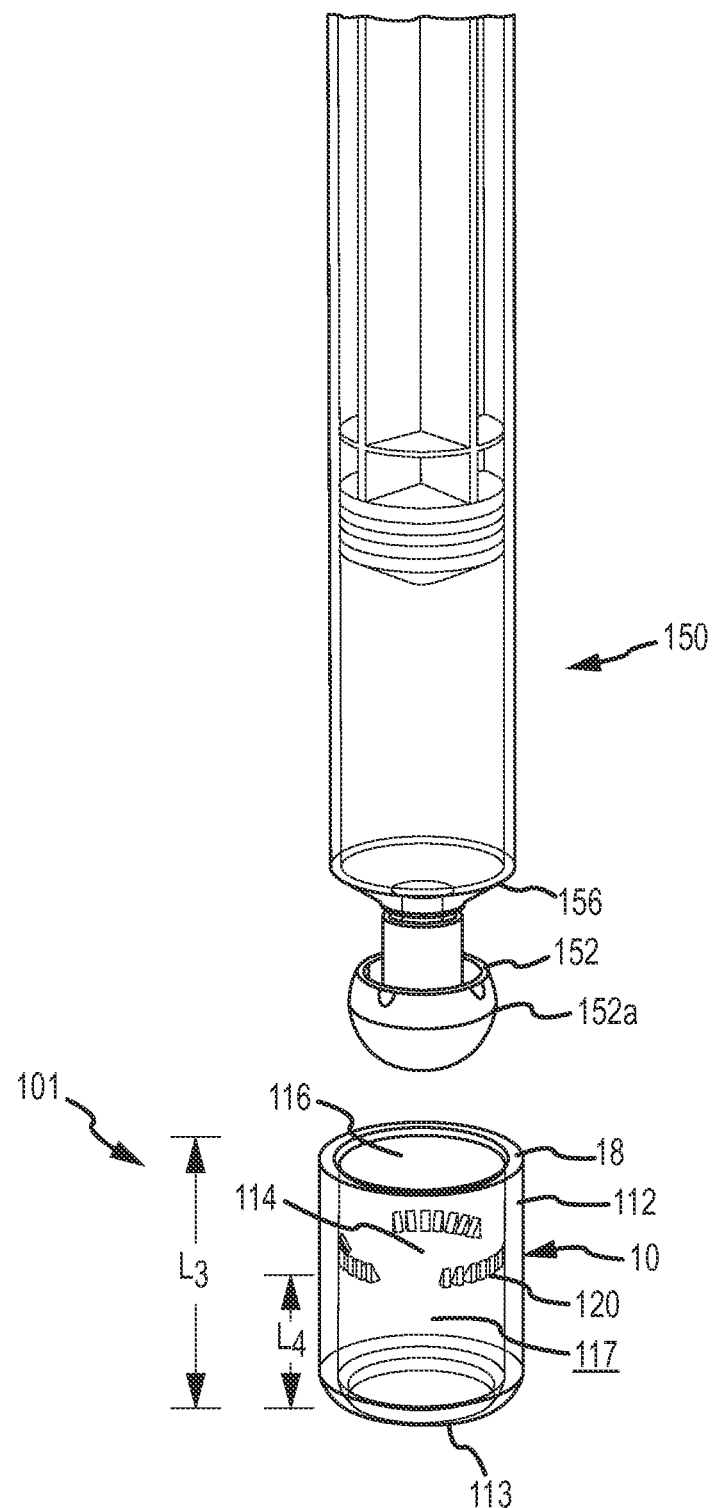
FIG. 7 illustrates the embodiment of FIG. 6 with the cap positioned on the corresponding oral dispenser.

As best shown in FIG. 7, the frame member 110 may define an encompassed or internal area 114 having a length $L_3$. Further, the frame member 110 may comprise an opening 116 to the encompassed or internal area 114 for receiving the cap 152 after positioning the cap 152 on the port 154 of dispenser 150.

Figure 8:
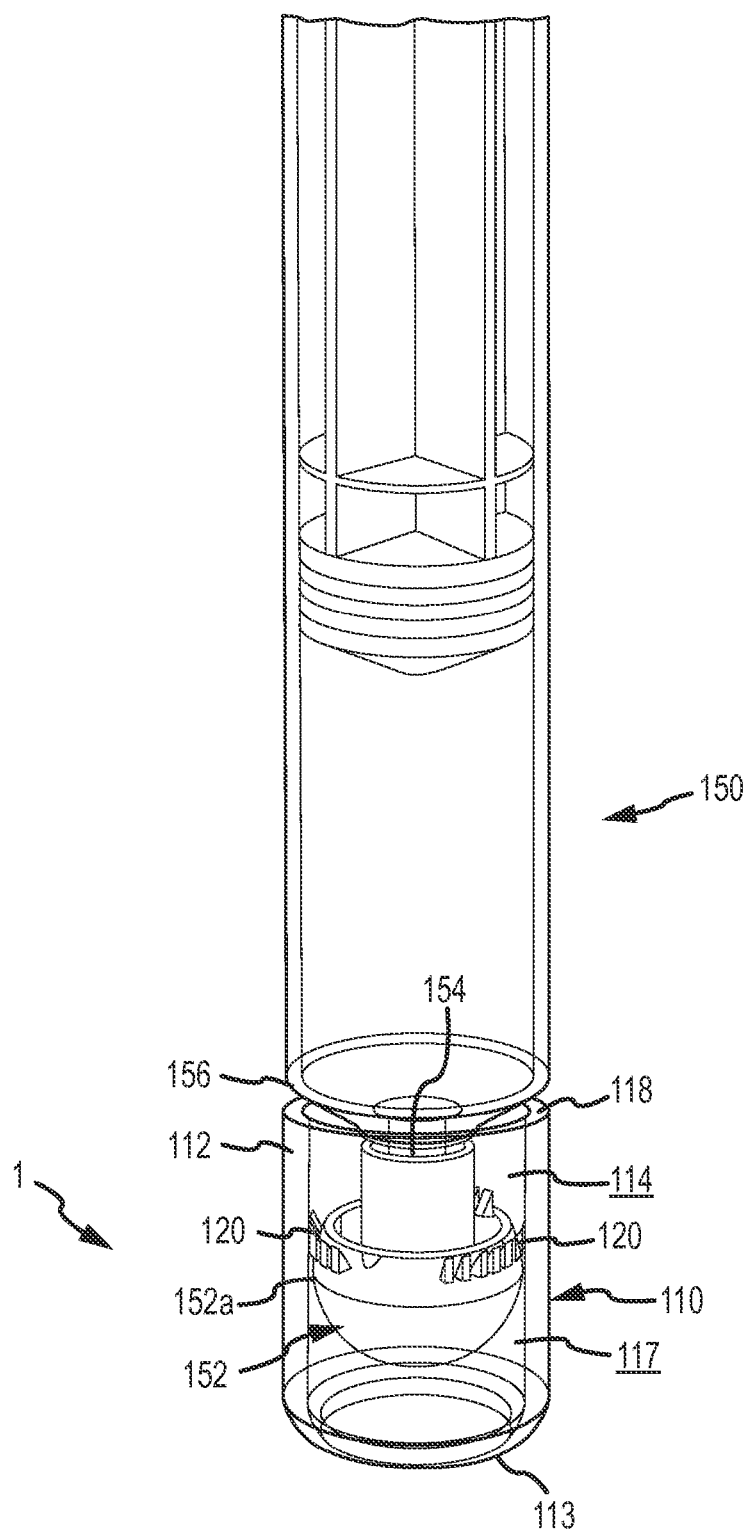
FIG. 8 illustrates the embodiment of FIG. 6 with the cap positioned on the corresponding oral dispenser captured by the anti-tampering apparatus.

In turn, the retention member(s) 120 may define a capture region 117 having a length $L_4$. In this regard, the retention member(s) 120 may be provided so that, after placement of cap 152 on port 154 of dispenser 150, as shown in FIG. 7, at least a portion of cap 152 may be forcibly advanced past the retention member(s) 120 in a first direction and retainably captured within the capture region 117, as shown in FIG. 8. In this regard, at least a portion of retention member(s) 120 and/or frame 110 and/or cap 152 may resiliently flex, or elastically deform, during cap capture. In the latter regard, the retention member(s) 120 may be located to restrict movement of the cap 152 in a second direction opposite to the first direction.

Figure 9:
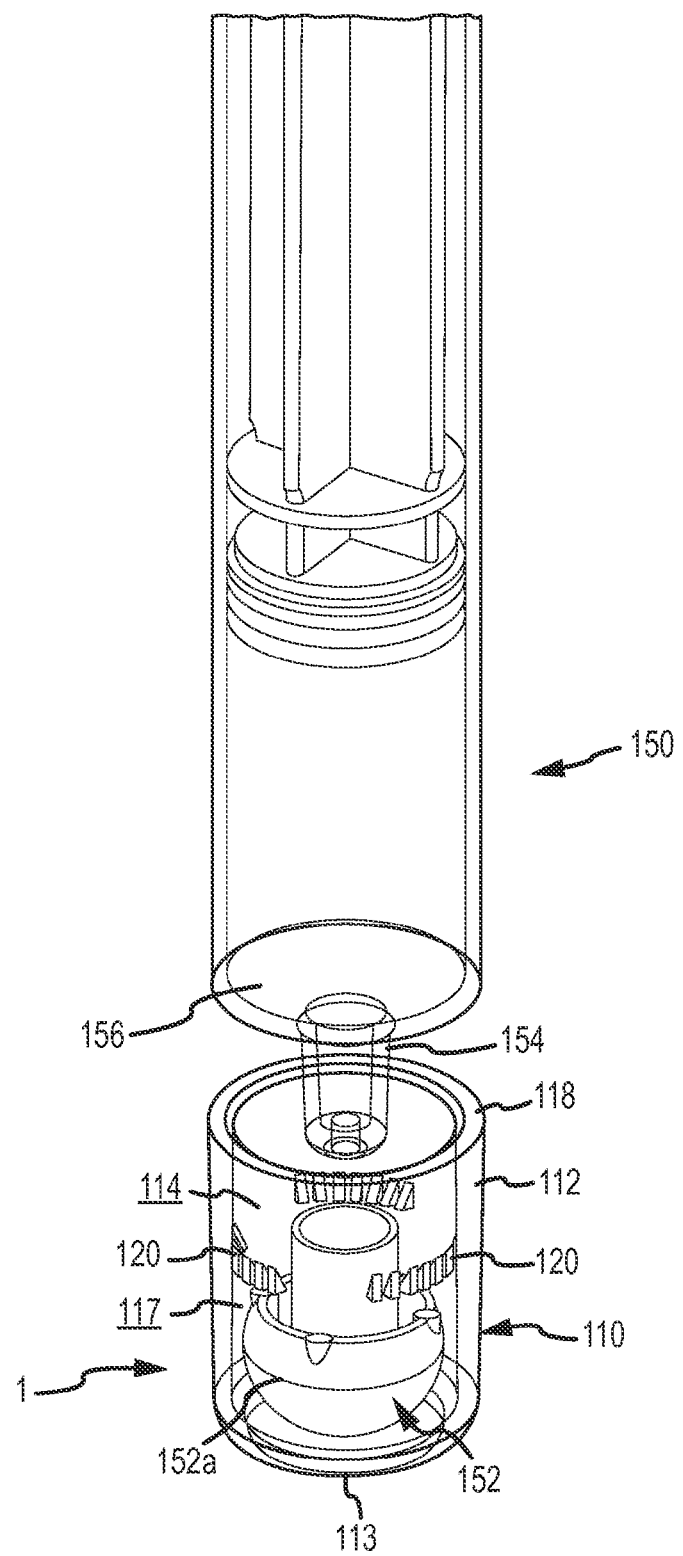
FIG. 9 illustrates the embodiment of FIG. 6 with the captured cap removed from the corresponding oral dispenser.

After capture of at least a portion of cap 152 in capture region 117, dispenser 150 and/or anti-tampering apparatus 101 may be moved relative to the other, e.g., dispenser 150 may be retracted in the second direction while anchoring anti-tampering apparatus 101, wherein captured cap 152 may be removed from port 154 of dispenser 150, as shown in FIG. 9. In conjunction with removal of cap 152, rounded portion 152a thereof may engage and be restrainably retained within capture region 117 by retention member(s) 120. As may be appreciated, such cap removal may be completed in conjunction with intended procedures in which the liquid drug may be administered from dispenser 150 to an intended patient after removal of cap 152.

Figure 10:
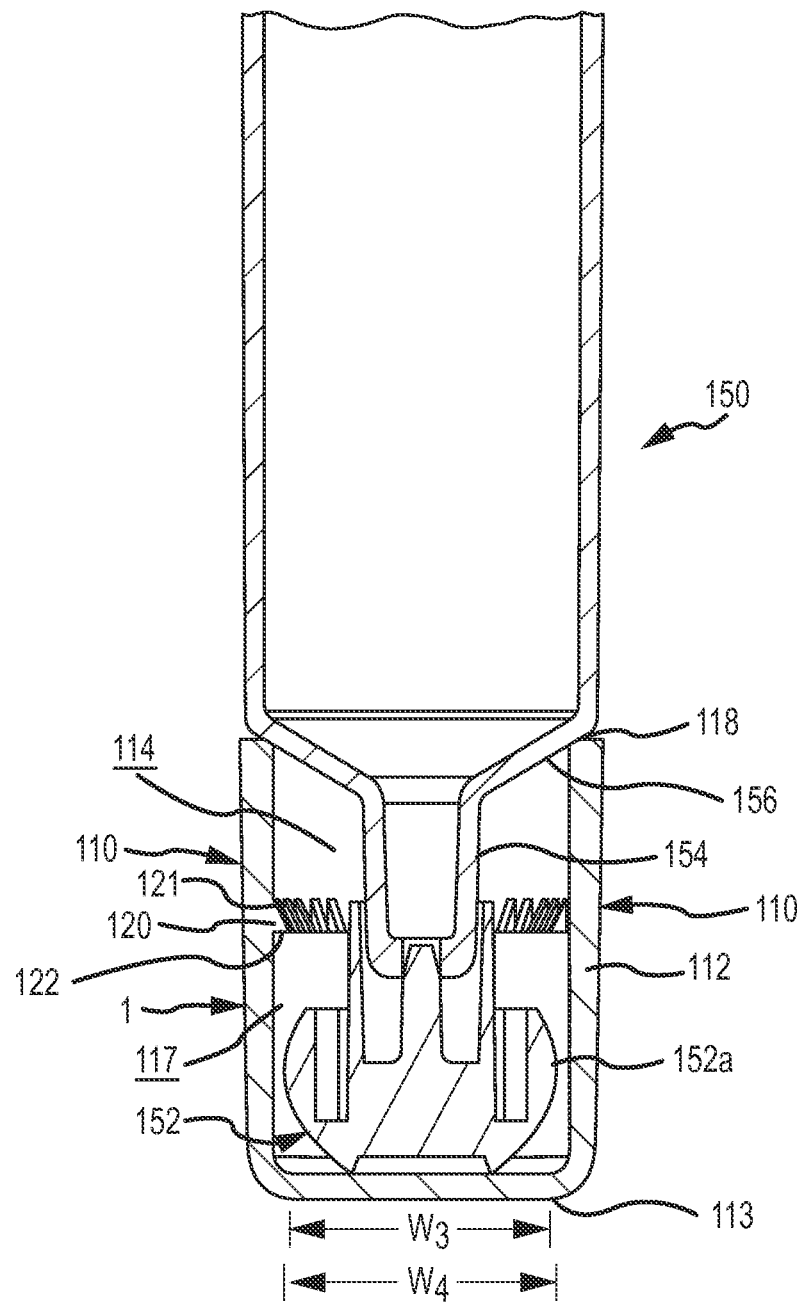
FIG. 10 is a cross-sectional view of the embodiment of FIG. 6, wherein recapping of the oral dispenser is obstructed by the anti-tampering apparatus.

As illustrated in FIG. 10, the retention member(s) 120 may be of a barb-like configuration, wherein the retention member(s) 120 includes a tapered surface 121 and ledge surface 122. The retention member(s) 120 may be disposed to restrainably engage rounded portion 152a of cap 152 at ledge surface 122 when captured cap 152 is moved toward opening 116. By way of example, retention member(s) 120 may define a minimum cross-dimension $W_3$ of encompassed area 114 that is less than a maximum cross-dimension $W_4$ of cap 152. In the illustrated embodiment, the maximum cross-dimension $W_4$ of cap 152 may be defined by a peripheral rounded portion 152a of cap 152 defining a maximum diameter thereof.

As further shown by FIG. 10, the anti-tampering apparatus 101 may be provided so that once cap 152 is captured in capture region 117 of anti-tampering apparatus 101, and cap 152 is removed from port 154 of the dispenser 150, the anti-tampering apparatus 101 may obstruct any attempt to recap the port 154 with the captured cap 152. In this regard, the frame member 110 may comprise a cylindrical edge surface 118 on sidewall 112 surrounding opening 116. The edge surface 118 may be located to obstruct recapping of dispenser 150 after capture of cap 152 within the capture region 117 and removal of cap 152 from port 154 of dispenser 150. Specifically, after removal of cap 152, edge surface 118 may engage a barrel surface 156 of the dispenser 150 to obstruct recapping of port 154. Concomitantly, cap 152 may assume a position in a rearward portion of the capture region 117, as shown in FIG. 10.

In the embodiment shown in FIGS. 6-10, oral dispenser 150 may comprise a barrel (e.g., having volumetric gradations, or indicia, thereupon), and plunger disposed therein for selective dispensation of predetermined amounts of a liquid drug (e.g., a predetermined unit dosage amount). Dispenser 150 may be of a type having a port 154 adapted for forcible, slip-on placement of cap 152. In this regard, dispenser 150 may be of a type utilized for oral dispensation of liquid medication. As shown in FIG. 10, cap 152 may include a shaft-like inner member 152b surrounded by an annular outer collar 152c to define an annular region therebetween. The inner member 152b may be sized for mating engagement within an end opening of port 154, and port 154 may be received within the annular region of cap 152, upon forcible slip-on placement of cap 152 on port 154.

Since positioning of cap 152 upon dispenser 150 may entail forcible advancement of port 54 relative to cap 152, cap 152 may assume a rearward position in capture region 117 upon any attempt to recap port 154 after removal of cap 152. In turn, any attempt to recap the dispenser 150 may be frustrated. As such, undesired tampering may be avoided since any unexpected absence of cap 152, as captured by anti-tampering apparatus 101, on port 154 of dispenser 150 would provide a definite indication that tampering has occurred.

FIGS. 11-15 correspond with yet another embodiment of an anti-tampering apparatus 201. The anti-tampering apparatus 201 is provided for use with a drug delivery device comprising a syringe 250 (e.g., a luer-lock syringe) and a slip-on cap 252 intended for positioning on port 254 of syringe 250. More particularly, the anti-tampering apparatus 201 may be provided to restrainably retain, or capture, cap 252. In one application, the syringe 250 may be filled with a drug in a liquid form prior to cap 252 placement on port 254 and capture by anti-tampering apparatus 201.

The anti-tampering apparatus 201 may comprise a frame member 210. Optionally, and as shown, frame member 210 may be at least partially transparent. The anti-tampering apparatus 201 may further include at least one retention member(s) 220 connected to the frame member 210 and disposed to capture cap 252. In addition, anti-tampering apparatus 201 may include at least one pivot member(s) 230 disposed to provide an obstruction surface(s) thereupon to restrict recapping of syringe 250 by cap 252 after capture of cap 252 within anti-tampering apparatus 201. In the illustrated embodiment, a plurality of retention members 220 and a plurality of pivot members 230 may project inwardly from a sidewall 212 of the frame 216.

The frame member 210, retention member(s) 220 may be integrally defined in a unitary anti-tampering apparatus embodiment. For example, anti-tampering apparatus 201 may be injection-molded from a polymer-based material. In some embodiments, the anti-tampering apparatus may comprise a polypropylene material or a stiffer polyethylene or polystyrene material.

In the illustrated embodiment, the frame member 210 is configured as a cap, with cylindrical sidewalls 212 and an end wall 213. In other embodiments, the frame member 210 may assume other configurations.

Figure 11:
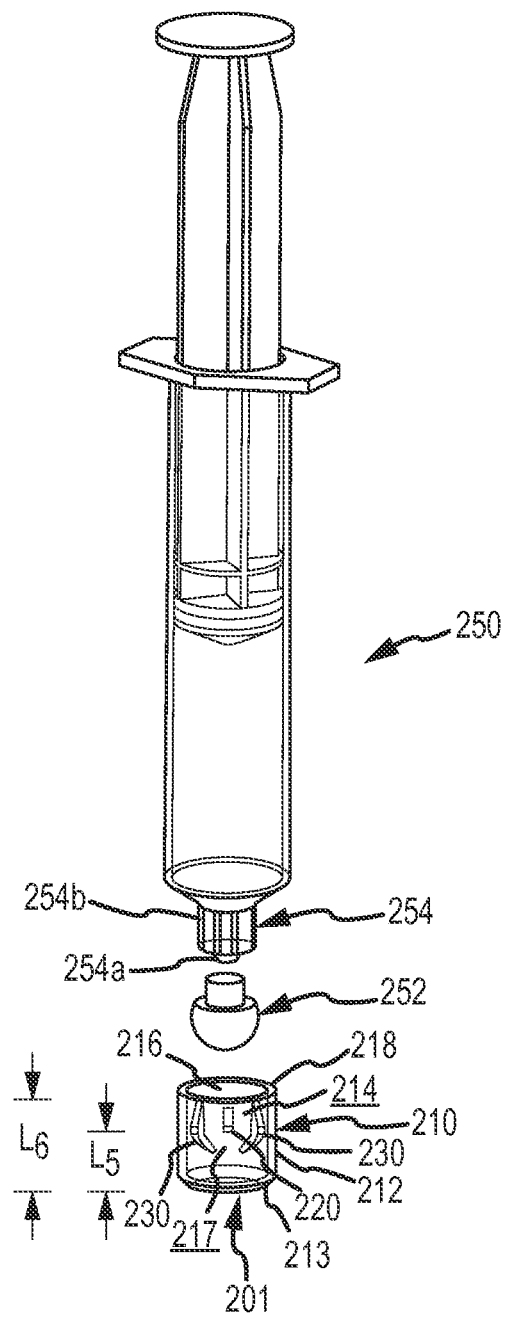
FIG. 11 illustrates an additional embodiment of an anti-tampering apparatus provided for use with a syringe and corresponding cap.

FIG. 11 illustrates the syringe 250 prior to capping of port 254 by cap 252, and prior to capture of cap 252 by anti-tampering apparatus 201. Such further capping and capture steps may be sequentially completed, as reflected by FIGS. 12, 13A and 13B. Further, such steps may be completed manually and/or in an automated manner by relative linear advancement of cap 252 and port 254 of syringe 250, and by relative linear advancement of capped syringe 250 and anti-tampering apparatus 201. In some applications, such steps may be completed in a single-stroke, linear movement of syringe 250. For example, cap 252 and anti-tampering apparatus 201 may be held in aligned positions (see, e.g., FIG. 11)

by a fixture and syringe may be linearly advanced in a first stroke segment to locate cap 252 on port 254. In turn, capped syringe 250 may be linearly advanced in a second stroke segment to capture the cap 252 of the capped syringe 250 within the anti-tampering apparatus 201.

As shown in FIG. 11, the frame member 210 may define an encompassed or internal area 214 having a length $L_6$. Further, the frame member 210 may comprise an opening 216 to the encompassed or internal area 214 for receiving the cap 252 after positioning the cap 252 on the port 254 of syringe 250.

Figure 12:
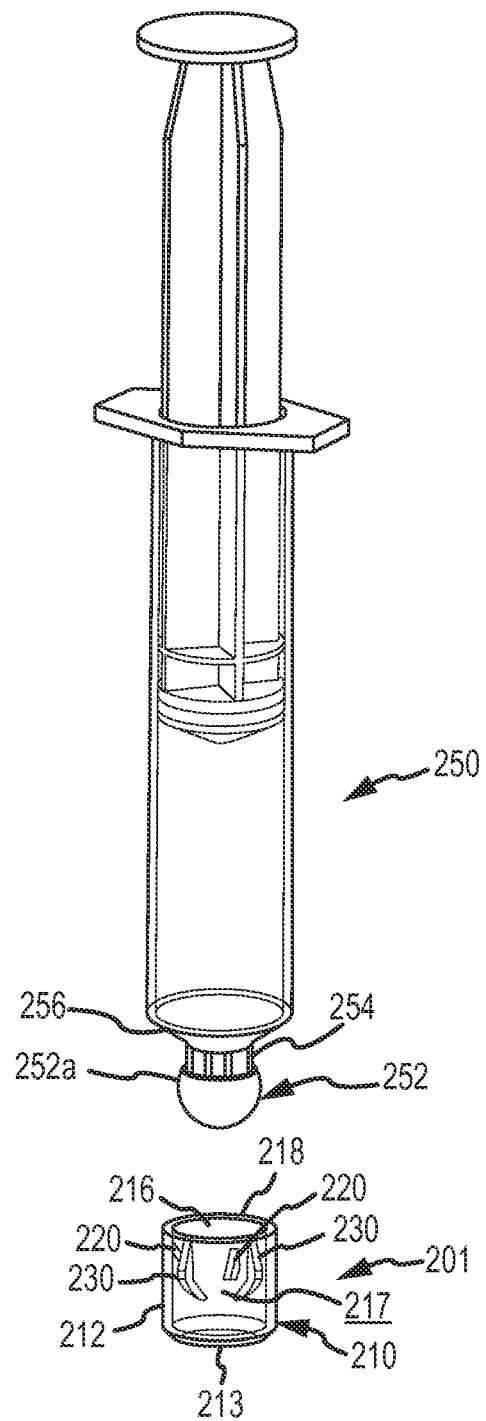
FIG. 12 illustrates the embodiment of FIG. 11 with the cap on the corresponding syringe.
Figure 13A:
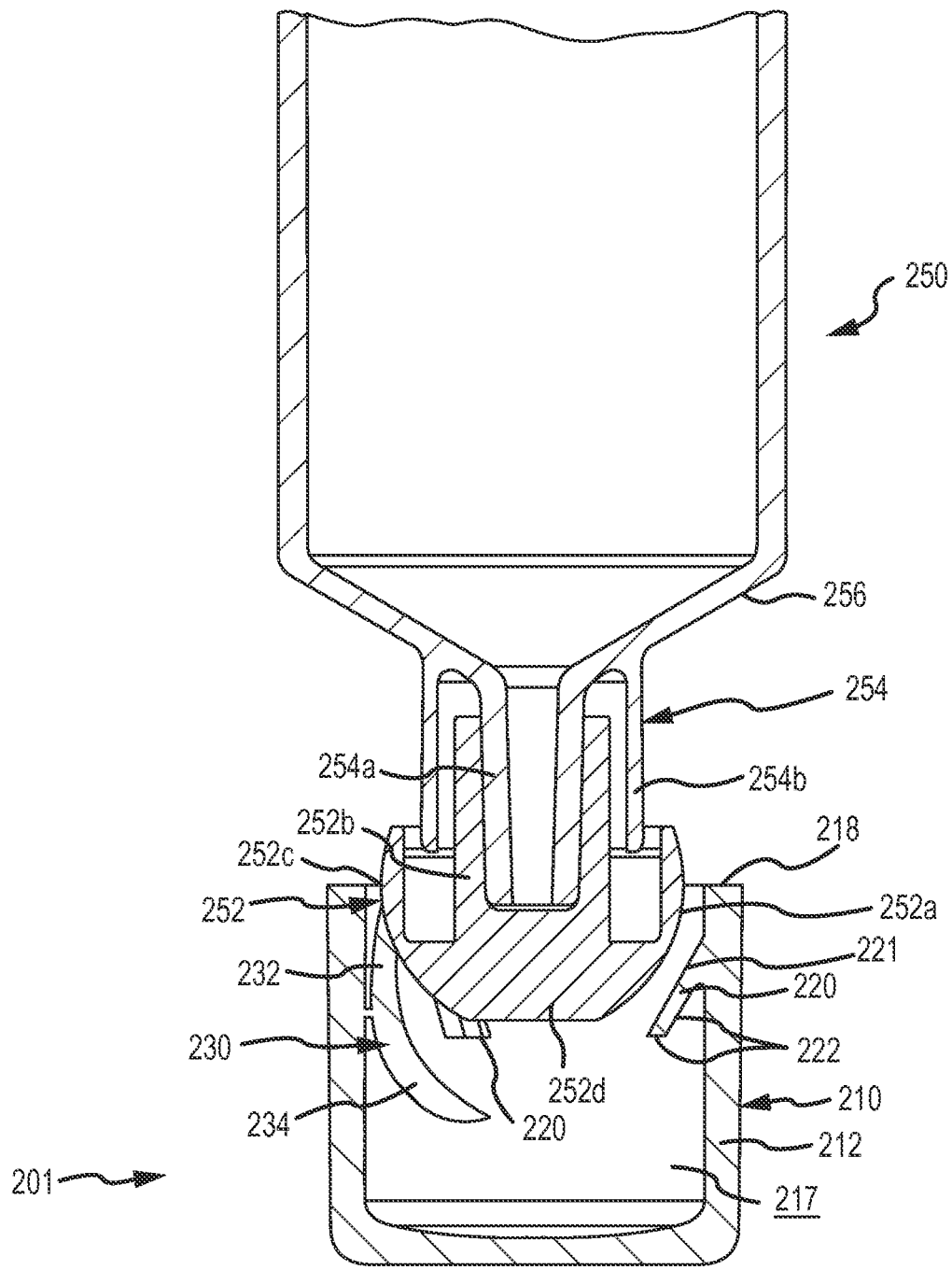
FIG. 13A is a cross-sectional view of the embodiment of FIG. 11 with the cap positioned on the syringe being inserted into the anti-tampering apparatus.
Figure 13B:
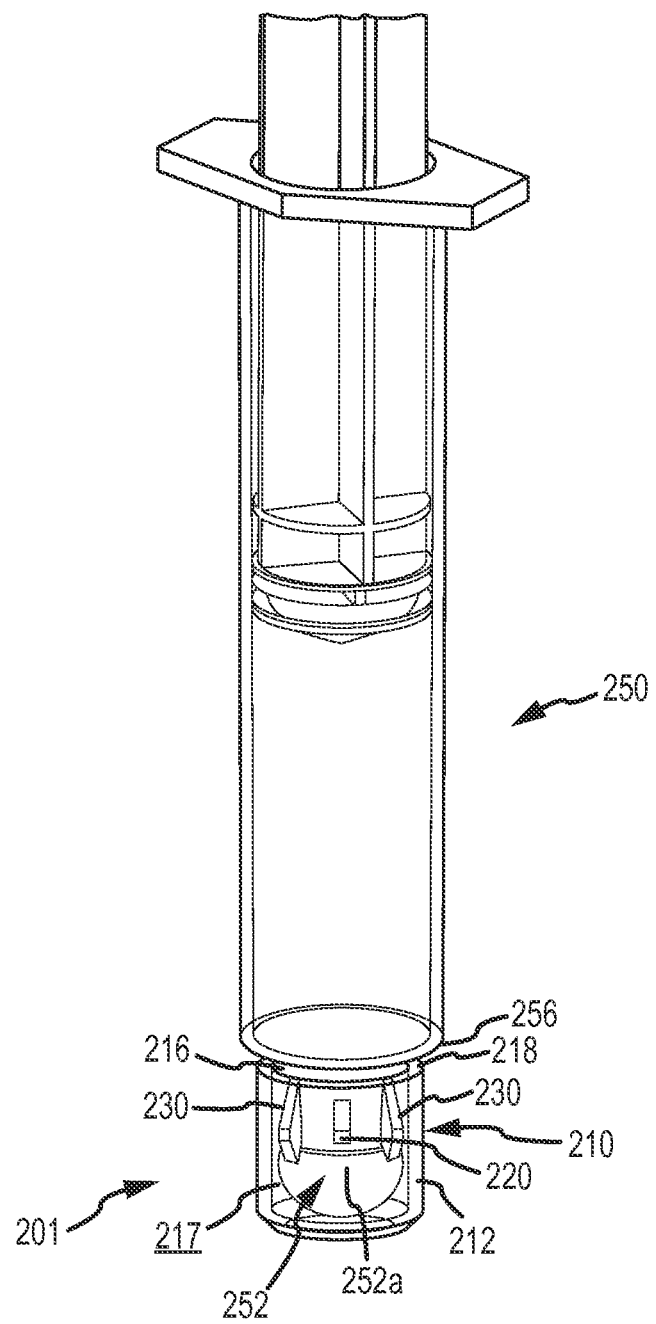
FIG. 13B illustrates the embodiment of FIG. 11 with the cap positioned on the syringe capture by the anti-tampering apparatus.

In turn, the retention member(s) 220 may define a capture region 217 having a length $L_5$. In this regard, the retention member(s) 220 may be provided so that, after placement of cap 252 on port 254 of syringe 250, as shown in FIG. 12, at least a portion of cap 252 may be forcibly advanced past the retention member(s) 220 in a first direction and retainably captured within the capture region 217. In this regard, at least a portion of retention member(s) 220 and/or frame 210 and/or cap 252 may resiliently flex, or elastically deform, during cap capture. FIG. 13A illustrates cap 254 on syringe 250 entering the anti-tampering apparatus 201, and FIG. 13B illustrates cap 252 captured within anti-tampering apparatus 201.

Figure 15:
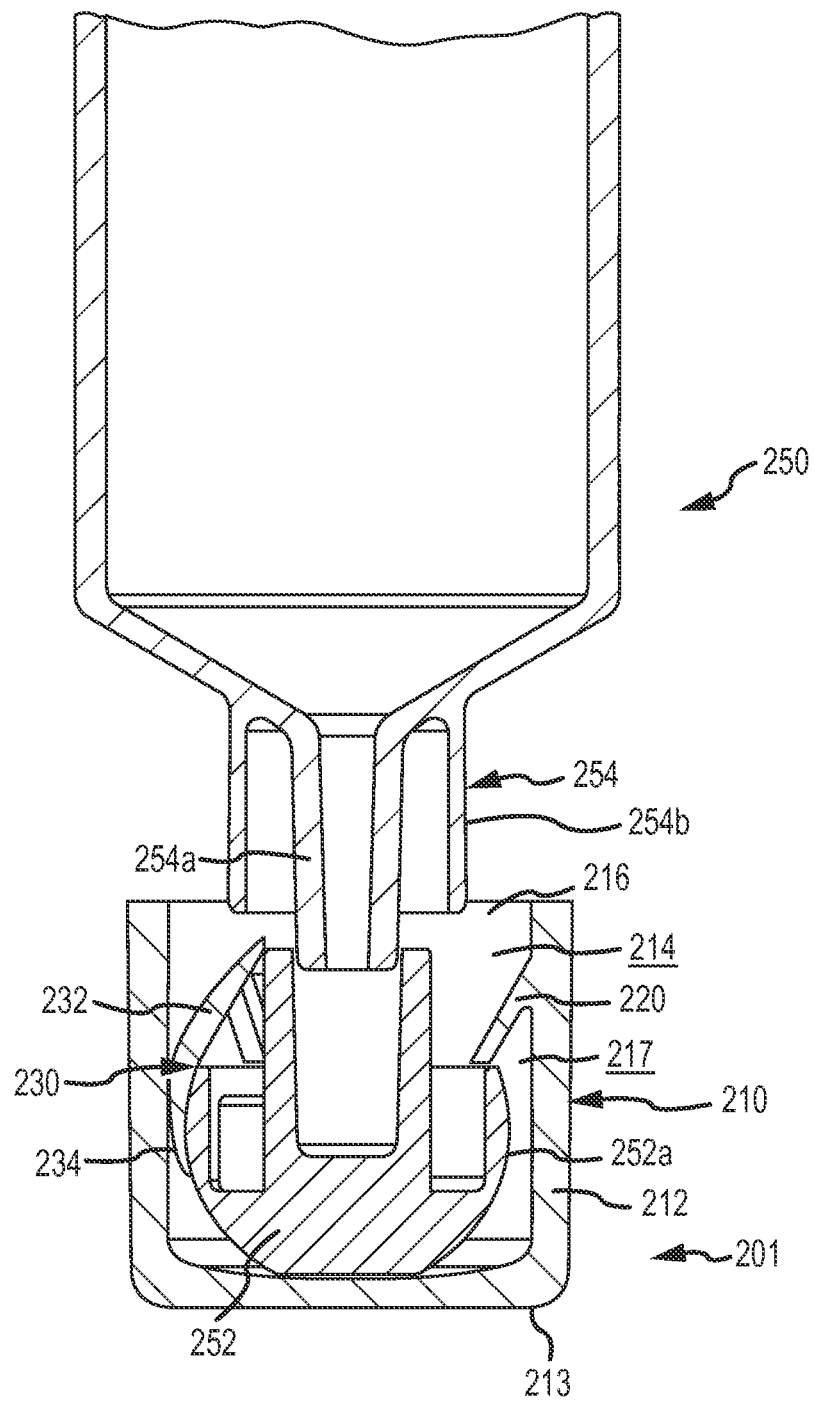
FIG. 15 is a cross-sectional view of the embodiment of FIG. 11, wherein recapping of the syringe is obstructed by the anti-tampering apparatus.

After capture of at least a portion of cap 252 in capture region 217, syringe 250 and/or anti-tampering apparatus 201 may be moved relative to the other, e.g., syringe 250 may be retracted in the second direction while anchoring anti-tampering apparatus 201, wherein captured cap 252 may be removed from port 254 of syringe 250, as shown in FIG. 15. In conjunction with removal of cap 252 rounded portion 252a thereof may engage and be restrainably retained within capture region 217 by retention member(s) 220. As may be appreciated, such cap removal may be completed in conjunction with intended procedures in which the liquid drug may be administered from syringe 250 to an intended patient after removal of cap 252.

As shown in FIG. 13A, the retention member(s) 220 may be of a barb-like configuration, wherein the retention member(s) 220 includes a tapered surface 221 and ledge surface 222. The retention member(s) 220 may be disposed to restrainably engage flange 252a of cap 252 at ledge surface 222 when captured cap 252 is moved toward opening 216. The retention member(s) 220 may be located to restrict movement of the cap 252 in a second direction opposite to the first direction. By way of example, retention member(s) 220 may define a minimum cross-dimension, or minimum diameter of a circular opening, within encompassed area 214 that is less than a maximum cross-dimension, or diameter, of cap 252. In the illustrated embodiment, the maximum cross-dimension of cap 252 may be defined by a periphery of rounded portion 252a of cap 252 defining a maximum diameter thereto.

As shown by FIG. 6, the anti-tampering apparatus 201 may be provided so that once cap 252 is captured in capture region 217 of anti-tampering apparatus 201, and cap 252 is removed from port 254 of the syringe 250, the anti-tampering apparatus 201 may obstruct any attempt to recap the port 254 with the captured cap 252.

In this regard, and as noted above, anti-tampering apparatus 201 may include pivot member(s) 230 for obstructing recapping of syringe 250 by cap 252 when captured in anti-tampering apparatus 201. To describe the operation of pivot member(s) 230, reference is made to FIGS. 13A, 14 and 15. As illustrated in FIG. 13A, pivot member(s) 230 may include a first portion 232 and a second portion 234 extending in different directions from a region of adjoinment to sidewall 212 of frame 210. More particularly, the first portion 232 may extend in a direction towards opening 216 and the second portion 234 may extend in a direction away from the opening 216.

Figure 14:
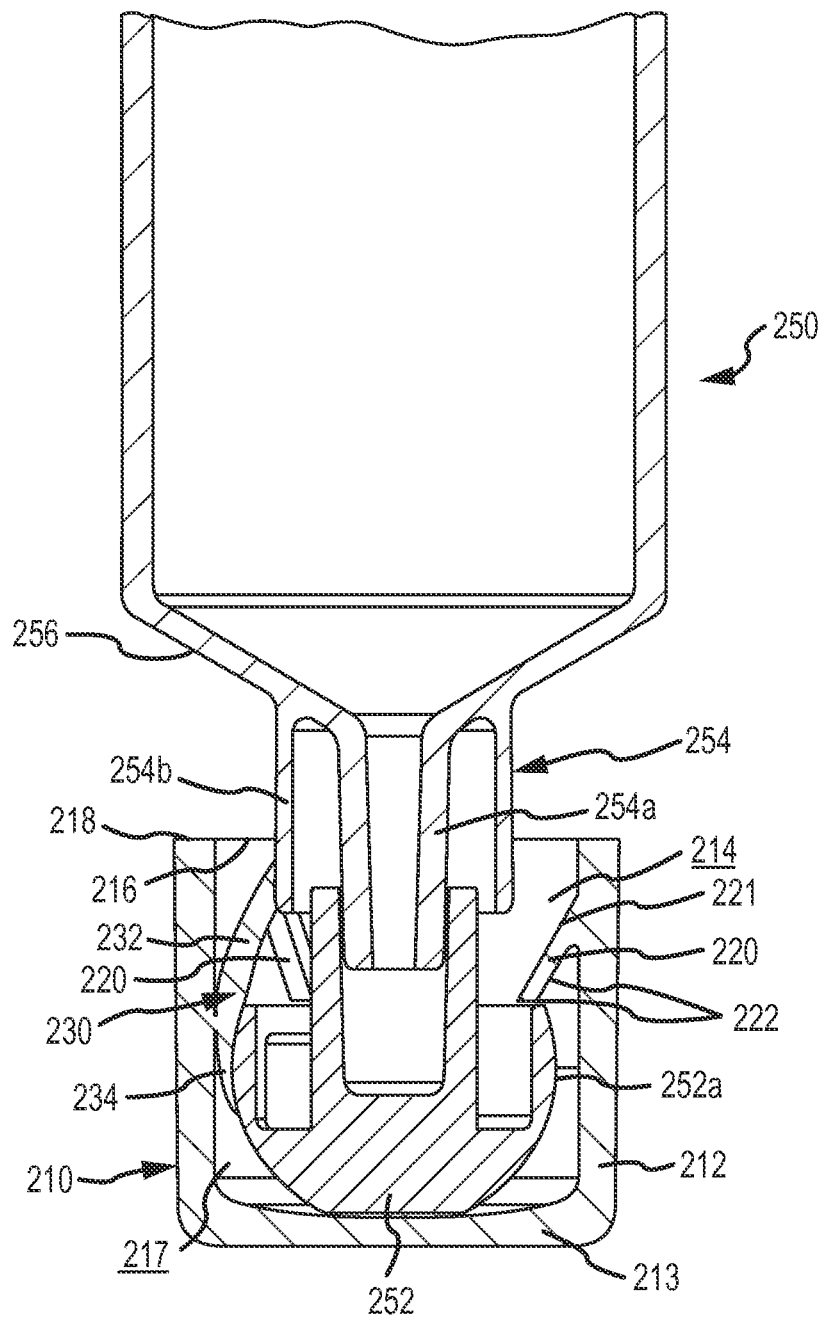
FIG. 14 is a cross-sectional view of the embodiment of FIG. 11 with the captured cap being removed from the corresponding syringe.

As shown in FIG. 13A, the pivot member(s) 230 may be in a first position prior to and at the outset of insertion of cap 252 into the anti-tampering apparatus 201. Then, as shown in FIG. 14, upon forced insertion of cap 252 into anti-tampering apparatus 201 the pivot member(s) may be disposed in a second position. More specifically, the second portion 234 may be pivot toward sidewall 212 and first portion 232 may be pivot away from sidewall 212. The pivot motion of first portion 232 may be limited by the presence of port 254 of syringe 250. In turn, and as shown in FIG. 15, upon removal of cap 252 from syringe 250, second portion 252 may further pivot away from sidewall 212. In turn, upon any attempt to recap syringe 250 with captured cap 252, second portion 252 of pivot member(s) 230 may engage the collar 254b of port 254 and thereby obstruct recapping.

In the embodiment shown in FIGS. 11-15, syringe 250 may comprise a barrel (e.g., having volumetric gradations, or indicia, thereupon) and a plunger disposed therein for selective dispensation of predetermined amounts of a liquid drug (e.g., a predetermined unit dosage amount). Syringe 250 may be of a type having a port 254 adapted for forcible, slip-on placement of cap 252. In this regard, syringe 250 may be of a type having a luer-lock connection arrangement at port 254, as shown in FIG. 12. For example, port 254 may include a nozzle 254a extending through and beyond a surrounding collar 254b. In turn, cap 252 may include an annular (e.g., cylindrical) inner collar 252b and an annular (e.g., cylindrical) outer collar 252c extending from an end wall 252d, wherein nozzle 254a may be forcibly advanced in a slip-on fashion into inner collar 252b of cap 252, and outer collar 254b of port 254 may be located in an annular region defined between inner collar 254b and outer collar 252c of cap 252.

The above-described anti-tampering apparatus embodiments 1, 101 and 201, and their corresponding drug delivery devices and caps, syringe 50/cap 52, oral dispenser 150/cap 152 and syringe 250/cap 252, respectively, may be provided as corresponding products and intended corresponding use. By way of example, in certain embodiments, anti-tampering apparatus 1 may be provided with indications that the anti-tampering apparatus 1 is compatible for use with syringes and caps of a type corresponding with syringe 50/cap 52. In other embodiments, anti-tampering apparatus 101 and 201 may be provided in corresponding relation to and/or with indications of compatibility with oral dispenser 150/cap 152 and syringe 250/cap 252. In either of the noted approaches, combinative products and associated methodologies may be advantageously employed in various embodiments of the present invention.

In the later regard, method embodiments may provide for handling of a drug delivery device (e.g., a syringe, oral dispenser or other drug delivery device) having a port, and a corresponding cap positionable on the port. In various embodiments, a method may include capturing a cap (e.g., 52, 152, 252) disposed on a port (e.g., 54, 154, 254) of a drug delivery device (e.g., 50, 150, 250) within an anti-tampering apparatus (e.g., 1, 101, 201), removing the cap (e.g., 52, 152, 252) from the port (e.g., 54, 154, 254) of the drug delivery device (e.g., 50, 150, 250), wherein the anti-tampering apparatus (e.g., 1, 101, 201) maintains capture of the cap (e.g., 52, 152, 252), and restricting repositioning of the cap (e.g., 52, 152, 252) onto the port (e.g., 54, 154, 254) of the drug delivery device (e.g., 50, 150, 250).

As may be appreciated, cap capture may be realized in various methods embodiments via utilization of retention member(s) (e.g., 20, 120 and 220) as described above. Further, restriction of repositioning of the cap onto the port of the corresponding drug delivery devices may be realized be the provision of obstruction surfaces (e.g., 18, 118 and surfaces of pivot members 230), as described in conjunction with the various embodiments hereinabove.

The noted methodology may be readily integrated into overall processes for handling of drug delivery devices. For example, drug delivery devices such as syringe 1, oral dispenser 101 and/or syringe 201, together with their corresponding caps 52, 152 and 252, may be packaged at a first production and/or assembly facility. In this regard, the drug delivery devices and associated caps may be packaged in the same or different enclosures and sterilized at the production facility. Further, the anti-tampering apparatus may be packaged at the same or a related production and/or assembly facility. Packaging for the drug delivery devices, corresponding caps and anti-tampering apparatus' may include markings or other indicia regarding compatibility for combinative use. In turn, the corresponding drug delivery devices and caps, and the anti-tampering apparatus, may be transported together or separately to users at medical care locations. By way of primary example, such products may be delivered to pharmacies located at hospitals and other medical care facilities.

Once delivered, the drug delivery devices and caps, and the anti-tampering apparatus, may be unpackaged for use at such facilities. For example, after unpackaging, the drug delivery devices may be filled with liquid medications corresponding with the type and nature of each given drug delivery device. Moreover, such filling may be completed on a patient specific basis within pharmacies associated with each given medical care facility. Further, the filled drug delivery devices may be capped with their corresponding caps. Then the caps of the capped drug delivery devices may be captured by the anti-tampering apparatus as described herein. In some applications, filling of the drug delivery devices, capping of the drug and cap capturing may be carried out manually. In other applications, such steps may be completed in automated fashion at medical care facilities.

In any case, after capture within anti-tampering apparatus, removal of a captured cap from a given drug delivery device may be completed in a manual manner by medical personnel attendant to the administration of a liquid medication to a patient. For example, the anti-tampering apparatus and drug delivery device may be anchored by different hands of a user, wherein relative movement of the hands may cause the port of the drug delivery device to retract out of the opening of the drug delivery device and disengage from the corresponding cap.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. A method for handling a drug delivery device comprising:

filling the drug delivery device with a predetermined amount of a liquid medication;

positioning a cap on a port of said drug delivery device after said filling step; and, capturing said cap disposed on said port of said drug delivery device within at least a portion of an anti-tampering apparatus, wherein said cap is non-removable from said anti-tampering apparatus after said capturing step.

2. A method as recited in claim 1, further comprising:

removing said cap from said port of said drug delivery device, wherein said anti-tampering apparatus maintains capture of said cap; and, restricting repositioning of said cap onto said port of said drug delivery device.

3. A method as recited in claim 2, wherein said restricting step comprises:

providing an at least one obstructive surface on said anti-tampering apparatus located to engage a surface of said drug delivery device and thereby obstruct repositioning of the cap on said port of said drug delivery device.

4. A method as recited in claim 3, wherein said at least one obstruction surface is located in an initial position prior to said capturing step, and wherein said at least one obstruction surface is automatically located in an obstruction position different from said initial position after said removing step.

5. A method as recited in claim 4, further comprising:

first moving said at least one obstruction surface from said initial position to another position in response to said capturing step; and, second moving said at least obstruction surface from said another position to said obstruction position in response to said removing step.

6. A method as recited in claim 4, wherein said at least one obstruction surface is located on a pivot member interconnected to a frame of said anti-tampering apparatus, and further comprising:

pivoting said pivot member relative to said frame to at least partially position said obstruction surface from said initial position to said obstruction position in response to said capturing step.

7. A method as recited in claim 6, wherein at least a portion of at least one of said pivot member and/or said frame is elastically deformed after said capturing step and prior to said removing step, wherein said pivot member applies a spring force against said drug delivery device after said capturing step and prior to said removing step, and wherein the method further comprises:

advancing said obstruction surface to said obstruction position in conjunction with said removing step in response to said spring force.

8. A method as recited in claim 3, wherein said at least one obstruction surface and said cap are located in a first relative position after said capturing step and prior to said removing step, wherein said at least one obstruction surface and said cap are positioned or positionable in a second relative position after said removing step, and wherein said obstruction surface restricts repositioning of said cap onto said port of said drug delivery device when said obstruction surface and said cap are positioned in said second relative position.

9. A method as recited in claim 8, wherein said anti-tampering apparatus includes an opening and a capture region to receive and capture of said cap, respectively, and further comprising:

moving said cap within said capture region in a direction away from opening after said removing step to locate said cap and said obstruction surface in said second relative position.

10. A method as recited in claim 7, wherein at least a portion of said anti-tempering apparatus is elastically deformed to apply a spring force against said drug delivery device after said capturing step and prior to said removing step, and further comprising:
  moving said obstruction surface in conjunction with said removing step in response to said spring force, wherein said obstruction surface and said cap are automatically located in said second relative position.

11. A method as recited in claim 1, wherein said capturing step comprises:
  advancing at least a portion of said cap forcibly past at least one retention member provided on said anti-tampering apparatus, wherein said cap is restrainably disposed within a capture region of said anti-tampering apparatus.

12. A method as recited in claim 11, further comprising:
  flexing at least a portion of at least one of said cap and said anti-tampering apparatus during said capturing step.

13. A method as recited in claim 1, further comprising:
  advancing linearly said port of said drug delivery device to successively complete said positioning and capturing steps.

14. A method as recited in claim 13, wherein said advancing step is completed manually.

15. A method as recited in claim 13, wherein said advancing step is completed in an automated manner.

16. A method as recited in claim 1, further comprising:
  completing said filling step and said positioning step at a first location; and,
  removing said cap from said port of said drug delivery device at a second location, remote from said first location, wherein said anti-tampering apparatus maintains capture of said cap.

17. A method as recited in claim 16, further comprising:
  completing said capturing step at said first location; and,
  labeling said drug delivery device at said first location to provide an identification indication corresponding with at least one of said liquid medication and a corresponding intended recipient of said liquid medication.

18. A method as recited in claim 16, further comprising:
  completing said capturing step at said second location.

19. A method as recited in claim 1, further comprising:
  packaging said drug delivery device and said cap at a first location.

20. A method as recited in claim 19, further comprising:
  sterilizing said drug delivery device and said cap at said first location.

21. A method as recited in claim 19, further comprising:
  unpackaging said drug delivery device and said cap at a second location, remote from said first location.

22. A method as recited in claim 18, further comprising:
  completing said filling step, said positioning step, and said capturing step at said second location.

23. A method as recited in claim 22, further comprising:
  providing said anti-tampering apparatus to said second location separate from said drug delivery device and said cap.

* * * * *